(12) United States Patent
Wu et al.

(10) Patent No.: US 9,796,673 B2
(45) Date of Patent: Oct. 24, 2017

(54) L-TARTRATE SALT OF PRIDOPIDINE

(71) Applicants: Raeann Wu, Montville, NJ (US); Ralph Curtis Haltiwanger, West Chester, PA (US); Stephen Bierlmaier, Thorndale, PA (US); Mehran Yazdanian, Philadelphia, PA (US)

(72) Inventors: Raeann Wu, Montville, NJ (US); Ralph Curtis Haltiwanger, West Chester, PA (US); Stephen Bierlmaier, Thorndale, PA (US); Mehran Yazdanian, Philadelphia, PA (US)

(73) Assignee: TEVA PHARMACEUTICALS INTERNATIONAL GMBH, Jona (CH)

( * ) Notice: Subject to any disclaimer, the term of this patent is extended or adjusted under 35 U.S.C. 154(b) by 0 days.

(21) Appl. No.: 14/975,248

(22) Filed: Dec. 18, 2015

(65) Prior Publication Data

US 2016/0176821 A1 Jun. 23, 2016

Related U.S. Application Data

(66) Substitute for application No. 62/095,382, filed on Dec. 22, 2014.

(51) Int. Cl.
*C07D 211/24* (2006.01)
*C07C 59/255* (2006.01)
*C07C 51/41* (2006.01)

(52) U.S. Cl.
CPC .......... *C07D 211/24* (2013.01); *C07C 51/412* (2013.01); *C07C 59/255* (2013.01)

(58) Field of Classification Search
None
See application file for complete search history.

(56) References Cited

U.S. PATENT DOCUMENTS

| | | | |
|---|---|---|---|
| 6,903,120 B2 | 6/2005 | Sonesson et al. | |
| 7,417,043 B2 | 8/2008 | Sonesson et al. | |
| 7,923,459 B2 | 4/2011 | Gauthier et al. | |
| 9,006,445 B2 | 4/2015 | Sonesson et al. | |
| 9,012,476 B2 | 4/2015 | Zimmermann et al. | |
| 9,139,525 B2 | 9/2015 | Wikström | |
| RE46,117 E | 8/2016 | Sonesson et al. | |
| 2003/0100547 A1 | 5/2003 | Dwoskin et al. | |
| 2009/0318500 A1 | 12/2009 | Trewartha et al. | |
| 2010/0076024 A1 | 3/2010 | Zimmermann et al. | |
| 2010/0197712 A1* | 8/2010 | Carlsson | A61K 31/435 514/277 |
| 2013/0150406 A1* | 6/2013 | Zimmermann | A61K 31/451 514/317 |
| 2013/0197031 A1 | 8/2013 | Sonesson | |
| 2013/0267552 A1 | 10/2013 | Waters et al. | |
| 2014/0088140 A1 | 3/2014 | Hayden | |
| 2014/0088145 A1 | 3/2014 | Hayden | |
| 2014/0378508 A1 | 12/2014 | Bassan et al. | |
| 2015/0202302 A1 | 7/2015 | Licht et al. | |
| 2015/0209344 A1 | 7/2015 | Zimmermann et al. | |
| 2015/0209346 A1 | 7/2015 | Hayden | |
| 2015/0216850 A1 | 8/2015 | Hayden | |
| 2015/0374677 A1 | 12/2015 | Schmidt et al. | |
| 2016/0095847 A1 | 4/2016 | Sonesson | |
| 2016/0166559 A1 | 6/2016 | Sonesson | |
| 2016/0176821 A1 | 6/2016 | Wu et al. | |
| 2016/0243098 A1 | 8/2016 | Geva et al. | |

FOREIGN PATENT DOCUMENTS

| | | |
|---|---|---|
| WO | WO 95/17385 | 5/1995 |
| WO | WO 2011/014003 A2 | 2/2011 |
| WO | WO 2011/107583 A1 | 11/2011 |
| WO | WO 2012/078591 A1 | 6/2012 |
| WO | WO 2016/138135 | 9/2016 |

OTHER PUBLICATIONS

Kilomentor at www.kilomentor.com/2008/02/the-complete-blog-for-the-preparation-of-pharmaceutical-salts (posted Feb. 11, 2008).*
Morissette et al. In Advanced Drug Delivery Reviews 56 (2004) 275-300.*
Kassaian in Tartaric Acid published in Ullmann's Encyclopedia of Industrial Chemistry (published online: Jun. 15, 2000 at http://onlinelibrary.wiley.com/doi/10.1002/14356007.a26_163/full) (retrieved from the internet Jan. 9, 2017).*
Furazolium tartrate at https://chem.nlm.nih.gov/chemidplus/name/furazolium%20tartrate%20%5Busan%5D (retrieved from the Internet Jan. 9, 2017).*
'Potassium L-tartrate monobasic' at http://www.sigmaaldrich.com/catalog/product/aldrich/243531?lang=en&region=US (retrieved from the internet Jan. 9, 2017).*
Haynes in Pharmaceutical Sciences, 94(10), pp. 2111-2120 (2006).*
Bastin et al. In Organic Process Research & Development 2000, 4, 427-435.*
House, D.W. at https://seekingalpha.com/news/3209503-tevas-huntingtons-disease-candidate-pridopidine-fails-beat-placebo-mid-stage-trial-positive (retrieved from the internet Jun. 15, 2017).*
Carrol, J. at https://en.hdbuzz.net/227 (retrieved from the internet Jun. 15, 2017).*
Huntington Study Group in Movement Disorders 28(10):1407-15 (2013).*
Oct. 13, 2009 International Preliminary Report on Patentability and Written Opinion of the International Search Authority for PCT International Application No. PCT/SE2008/050414 (WO 2008/127188 A1), published Oct. 23, 2008 (Wikström).
International Preliminary Report on Patentability issued Jun. 10, 2014 including Notification of Transmittal of the International Search Report and the Written Opinion of the International Searching Authority, or the Declaration, including an International Search Report and Written Opinion of the International Searching Authority, mailed Feb. 22, 2013 in connection with PCT International Application No. PCT/US2012/68582 filed Dec. 7, 2012.

(Continued)

*Primary Examiner* — Dennis Heyer
(74) *Attorney, Agent, or Firm* — John P. White; Cooper & Dunham LLP

(57) ABSTRACT

The subject invention provides pridopidine L-tartrate, compositions and a process for manufacture thereof.

19 Claims, 11 Drawing Sheets

(56) References Cited

OTHER PUBLICATIONS

Apr. 30, 2015 European Search Report for European Patent Application No. 1285545.4.
Apr. 23, 2012 Office Action in connection with U.S. Appl. No. 12/595,472.
Jul. 23, 2012 Response to Apr. 23, 2012 Office Action in connection with U.S. Appl. No. 12/595,472.
Sep. 18, 2012 Office Action in connection with U.S. Appl. No. 12/595,472.
Mar. 12, 2013 Response to Sep. 18, 2012 Office Action in connection with U.S. Appl. No. 12/595,472.
Apr. 4, 2014 Office Action in connection with U.S. Appl. No. 12/595,472.
Jul. 7, 2014 Response to Apr. 4, 2014 Office Action in connection U.S. Appl. No. 12/595,472.
May 17, 2013 Office Action in connection with U.S. Appl. No. 13/708,816.
Aug. 16, 2013 Amendment in response to May 17, 2013 Office Action in connection with U.S. Appl. No. 13/708,816.
Nov. 5, 2013 Final Office Action issued in connection with U.S. Appl. No. 13/708,816.
Feb. 5, 2014 Response to Nov. 5, 2013 Final Office Action issued in connection with U.S. Appl. No. 13/708,816.
Mar. 11, 2014 Advisory Action issued in connection with U.S. Appl. No. 13/708,816.
May 5, 2014 Response to Nov. 5, 2013 Final Office Action and Mar. 11, 2014 Advisory Action in connection with U.S. Appl. No. 13/708,816.
Jun. 18, 2014 Office Action in connection with U.S. Appl. No. 13/708,816.
Sep. 18, 2014 Amendment in Response to Jun. 18, 2014 Office Action in connection with U.S. Appl. No. 13/708,816.
Oct. 22, 2012 Office Action issued by the European Patent Office in connection with European Patent Application No. 08 741 904.0.
Apr. 30, 2013 Response to Oct. 22, 2012 Office Action filed in connection European Patent Application No. 08 741 904.0.
Jun. 22, 2012 Office Action issued by the Australian Patent Office in connection with Australian Patent Application No. 2008239841.
Jun. 21, 2013 Response to Jun. 22, 2012 Office Action filed in connection with Australian Patent Application No. 2008239841.
Jul. 31, 2012 Office Action issued by the Israeli Patent Office in connection with Israeli Patent Application No. 201401 (translation).
May 24, 2013 Office Action issued by the Japanese Patent Office in connection with Japanese Patent Application No. 2010-502976 (with English Language translation).
Aug. 23, 2013 Response to May 24, 2013 Office Action filed in connection with Japanese Patent Application No. 2010-502976 (with English draft sent to Japanese associates for filing).
Feb. 21, 2012 First Office Action issued by the Mexican Patent Office in connection with Mexican Patent Application No. MX/a/2009/011020 (Translation).
Apr. 18, 2012 Response to Feb. 21, 2012 First Office Action filed in connection with Mexican Patent Application No. MX/a/2009/011020 (with Google TranslateTM translation of main text to English).
Aug. 22, 2012 Second Office Action filed in connection with Mexican Patent Application No. MX/a/2009/011020 (Translation).
Sep. 25, 2012 Response to Aug. 22, 2012 Second Office Action filed in connection with Mexican Patent Application No. MX/a/2009/011020 (with Google TranslateTM translation of main text to English).
Feb. 8, 2013 Third Office Action issued by the Mexican Patent Office in connection with Mexican Patent Application No. MX/a/2009/011020 (with Google TranslateTM translation of main text to English.
Apr. 29, 2013 Response to Feb. 8, 2013 Third Office Action filed in connection with Mexican Patent Application No. MX/a/2009/011020 (with English draft sent to Mexican associates for filing).
Jul. 26, 2011 First Office Action issued by the Chinese Patent Office in connection with Chinese Patent Application No. 200880017598.8 (with English Language translation).
Dec. 9, 2011 Response to Jul. 26, 2011 First Office Action filed in connection with Chinese Patent Application No. 200880017598.8 (with English Language translation of claims).
Feb. 22, 2012 Second Office Action issued by the Chinese Patent Office in connection with Chinese Patent Application No. 200880017598.8 (with English Language translation).
May 7, 2012 Response to Feb. 22, 2012 Second Office Action filed in connection with Chinese Patent Application No. 200880017598.8 (with English Language translation of claims).
Oct. 8, 2010 Office Action issued by the New Zealand Patent Office in connection with New Zealand Patent Application No. 580586.
Oct. 7, 2011 Response to Oct. 8, 2010 Office Action filed in connection with New Zealand Patent Application No. 580586.
Feb. 15, 2012 Office Action issued by the Russian Patent Office in connection with Russian Patent Application No. 2009141300/04(058696) (with English Language translation).
Jul. 13, 2012 Response to Feb. 15, 2012 Office Action filed in connection with Russian Patent Application No. 2009141300/04(058696) (with English Language translation of claims and Google TranslateTM translation of main text of Office Action to English).
Feb. 26, 2014 Office Action issued by the Canadian Patent Office in connection with Canadian Patent Application No. 2,683,719.
Feb. 3, 2014 Opposition filed against Venezuelan Patent Application No. 001610-2012 by CIFAR.
Apr. 22, 2014 response to Feb. 3, 2014 Opposition filed against Venezuelan Patent Application No. 001610-2012 by CIFAR.
Notification Concerning Transmittal of International Preliminary Report on Patentability (Chapter I of the Patent Cooperation Treaty), including an International Preliminary Report on Patentability and Written Opinion of the International Searching Authority, mailed Mar. 20, 2014 by the International Bureau of WIPO in connection with PCT International Application No. PCT/EP2012/067371, filed Sep. 6, 2012.
Nov. 19, 2014 Office Action issued by the Chinese Patent Office in connection with Chinese Patent Application No. 201280043794.9 (including English Language Translation of the cover pages).
Apr. 3, 2015 Response to Nov. 19, 2014 Office Action issued by the Chinese Patent Office in connection with Chinese Patent Application No. 201280043794.9 (including English Language Translation of the cover pages).
May 29, 2015 Office Action issued by the European Patent Office in connection with European Patent No. 12755869.0.
Sep. 25, 2015 Response to May 29, 2015 Office Action issued by the European Patent Office in connection with European Patent No. 12755869.0.
U.S. Appl. No. 15/052,368, Michal Geva et al., Unpublished.
U.S. Appl. No. 14/693,783, Sonesson et al.
Bruce J. Aungst and Nicole Matz. "Prodrugs to Reduce Presystemic Metabolism". Prodrugs. Challenges and Rewards Part 1. Ed. Valentino J. Stella, et al. New York: Springer, 2007. 339-355.
"Prodrug" definition, medical dictionary p. 1 (2004).
Rajsner et al., "4,4-Bis(4-Fluorophenyl)Butylamines and Their Cyclic Analogues; an Efficient sysnthesis of the Neuroleptic Penfluridol," Collection of Czechoslovak Chemical Communications, 1978, 43(7), pp. 1760-1777.
Testa "Prodrugs : bridging pharmacodynamic/pharmacokinetic gaps" Curr. Opion. Chem. Biol.v. 13 p. 338-344 (2009).
"Zolpidem tartrate" European Pharmacopoeia 5.0, pp. 2734-2735, date of access: Dec. 8, 2014.
R. Anton et al. "Opinion of the Scientific Panel on Food Additives, Flavourings, Processing Aids and Materials in Contact with Food (AFC) on a request from the Commission related to L-Carnitine-L-tartrate for use in foods for particular nutritional uses" The EFSA Journal (2003)19, 1-13.
Ohannesian et al., Handbook of Pharmaceutical Analysis, Marcel Dekker, 2002, New Yor—Basel.
Zimmermann et al., "Polymorphs of Pridopidine Hydrochloride" Cryst. Growth Des. 2012, 12, 2961-2968.
U.S. Appl. No. 15/217,806, Danit Licht et al., Unpublished.

(56) References Cited

OTHER PUBLICATIONS

U.S. Appl. No. 15/217,683, Offir Barel et al., Unpublished.
Apr. 12, 2016 Office Action issued in connection with Japanese Patent Application No. 2014-528965 (including English Language Translation).
Aug. 22, 2016 Office Action issued by the Mexico Patent Office in connection with Mexico Patent Application No. MX/a/2014/006664 (Including English Translation).
Jul. 29, 2016 Office Action issued by the European Patent Office in connection with European Patent Application No. 12855452.4.
Jul. 2016 Office Action issued by the Taiwanese Patent Office in connection with Taiwanese Patent Application No. 101146235 (including English Translation).
Sep. 6, 2016 Response to Jul. 2016 Office Action issued by the Taiwanese Patent Office in connection with ROC (Taiwan) Patent Application No. 101146235.
Oct. 12, 2016 Response to Examiner's Telephone Notification in connection filed with the Taiwanese Patent Office in connection with Taiwan Patent Application No. 101146235.
Jun. 14, 2016 Office Action issued by the Austrailian Patent Office in connection with Australian Patent Application No. 2012306386.
Aug. 17, 2016 Office Action issued by the Indian Patent Office in connection with Indian Patent Application No. 6397/CHENP/2009.
Berge, S et al. "Pharmaceutical Salts" 1977 Journ of Phrama Sciences; vol 66 No. 1 p. 1-16.

* cited by examiner

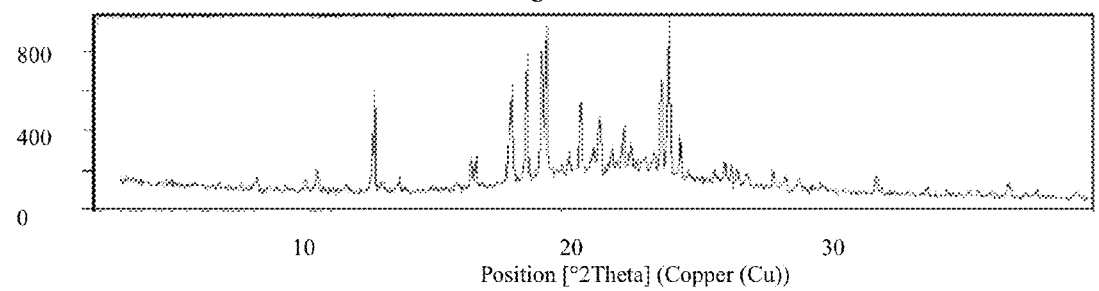
Figure 6d
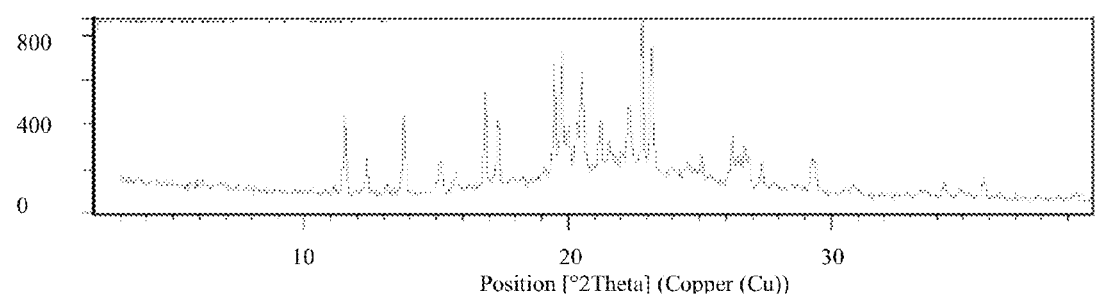
Figure 6e
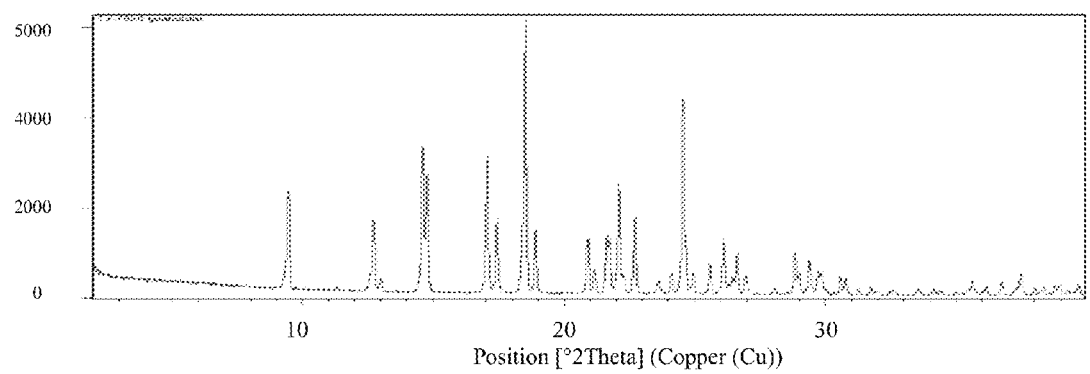
Figure 6f
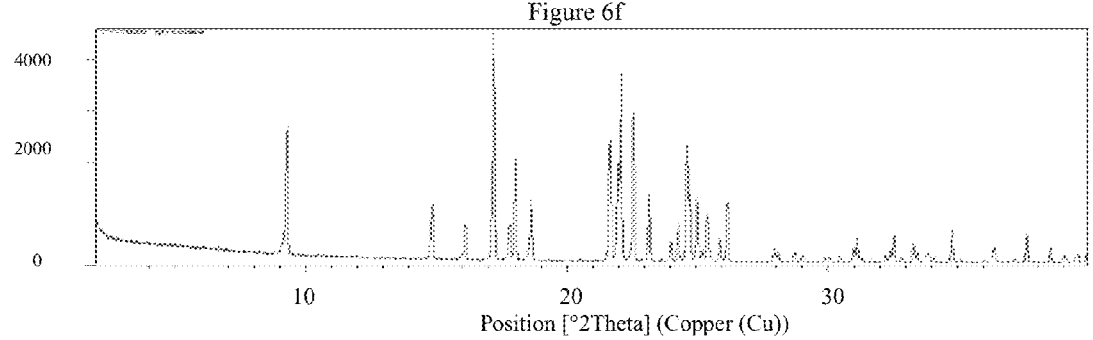

L-TARTRATE SALT OF PRIDOPIDINE

This application claims the benefit of U.S. Provisional Application No. 62/095,382, filed Dec. 22, 2014, the entire contents of which is hereby incorporated by reference herein.

Throughout this application, various publications are referred to by first author and year of publication. Full citations for these publications are presented in a References section immediately before the claims. Disclosures of the publications cited in the References section are hereby incorporated by reference in their entireties into this application in order to more fully describe the state of the art as of the date of the invention described herein.

BACKGROUND OF INVENTION

Pridopidine

Pridopidine (4-[3-(methylsulfonyl)phenyl]-1-propyl-piperidine) (Huntexil®, formerly known as ACR16) is a drug under development from a new class of pharmaceutical agents, the dopidines, which are considered to have dopaminergic stabilizing properties. Processes of synthesis of pridopidine are disclosed in U.S. Pat. No. 7,923,459. Dopaminergic stabilizers are compounds that can both enhance and counteract dopamine dependent functions in the central nervous system (CNS), depending on the initial level of dopaminergic activity. Dopaminergic stabilizers suppress the hyperactive behavior induced by stimulants such as amphetamine. In contrast, at low levels of dopamine function, the dopamine stabilizers enhance behavioral activity. The primary effect of pridopidine on HD-related motor symptoms is therefore expected to occur via the dopamine transmissions modulating properties of pridopidine. (Ponten 2010)

Huntington's Disease

Huntington's disease (HD) is a fatal neurodegenerative disorder with an autosomal dominant mode of inheritance. The disease is associated with a triad of motor, behavioral, and cognitive symptoms. Motor disturbances are the defining feature of the disease, with chorea the most evident motor symptom. Although useful for diagnosis, chorea is a poor marker of disease severity. Rather, disability and disease severity best correlate with negative motor features such as impairment in fine motor skills, bradykinesia, and gross motor coordination skills, including speech difficulties, gait, and postural dysfunction (Mahant 2003).

Dopamine is widely regarded as an important neurotransmitter modulating several aspects of brain functions including motor function. (Nieouilon 2003) A disrupted dopaminergic signaling has been implicated in a number of neurological and psychiatric conditions, (Zhan 2011, Dunlop 2007) and there is considerable clinical and preclinical evidence suggesting that dopaminergic functions are also compromised in HD. (Kung 2007, Huot 2007)

A number of medications are prescribed to ameliorate the motor and emotional problems associated with HD; however, the scientific evidence for the usefulness of various drugs in HD is poor, (Mestre 2009 CD006455, Mestre 2009 CD006456) Only 1 drug, tetrabenazine, which reduces dopamine availability and transmission, is registered specifically for the treatment of patients with HD for the management of chorea. No registered drugs are available for the management of the multifaceted motor symptoms. As such, there is a significant unmet medical need to develop medications to ameliorate symptoms of HD.

BRIEF SUMMARY OF THE INVENTION

The subject invention provides pridopidine L-tartrate.

The subject invention also provides a process for manufacture of pridopidine L-tartrate comprising:
  a) combining L-tartaric acid with pridopidine free base to form a mixture
  b) obtaining pridopidine L-tartrate from the mixture.

BRIEF DESCRIPTION OF THE SEVERAL VIEWS OF THE DRAWINGS

The present invention is further illustrated by reference to the accompanying drawings.

| Salt | FIG. |
|---|---|
| Besylate, Form A1 | 6a |
| Besylate, Form B1 | 6b |
| Fumarate, Form A1 | 6c |
| Fumarate, Form B1 | 6d (top) |
| Fumarate, Form C1 | 6d (bottom) |
| Gentistate Fumarate | 6e |
| Glycolate | 6f |
| L-malate | 6g |
| Napthalene 2-sulfonate | 6h |
| Oxalate | 6i |
| Succinate | 6j |
| Succinate (hemi) | 6k |
| Tosylate | 6l |
| — | — |

Figure 7:
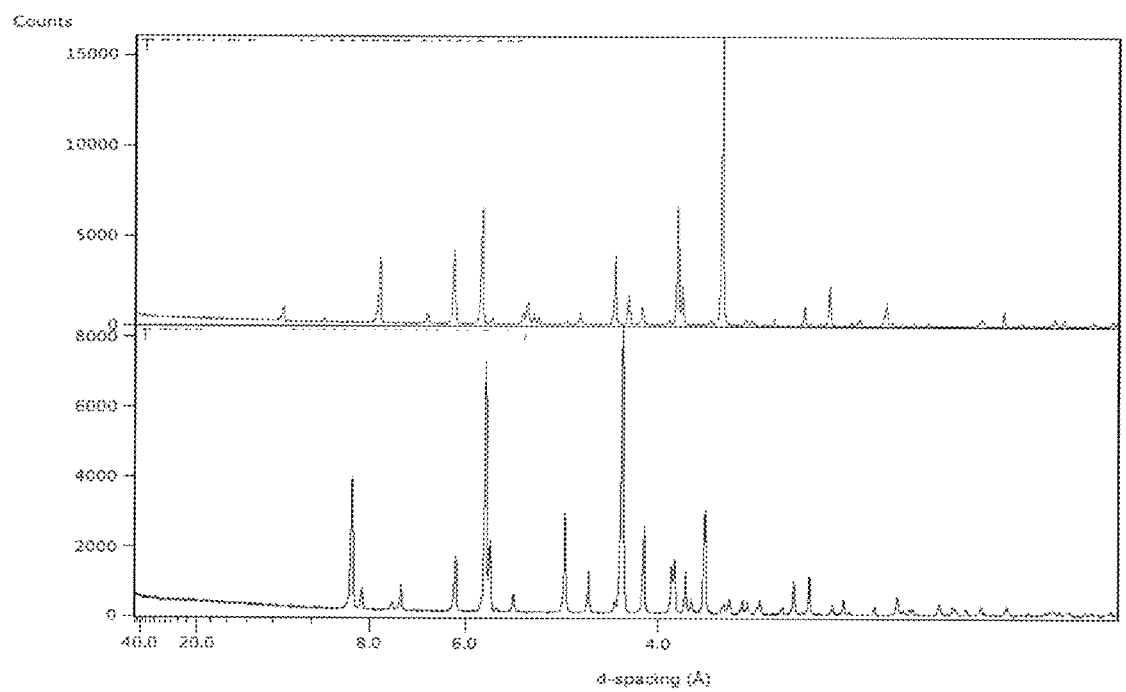

FIG. 7: XRPD showing d-spacing values of pridopidine hydrochloride and pridopidine mono L-tartrate side by side.

Figure 8:
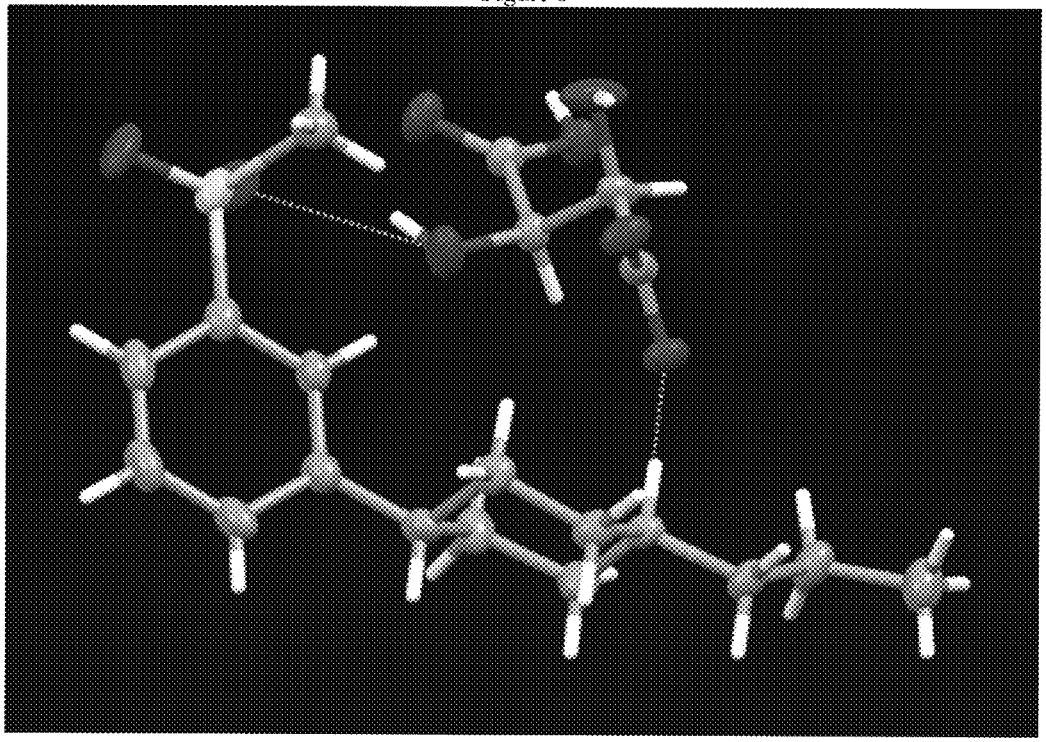

FIG. 8: The single crystal structure of pridopidine L-tartrate

Figure 9:
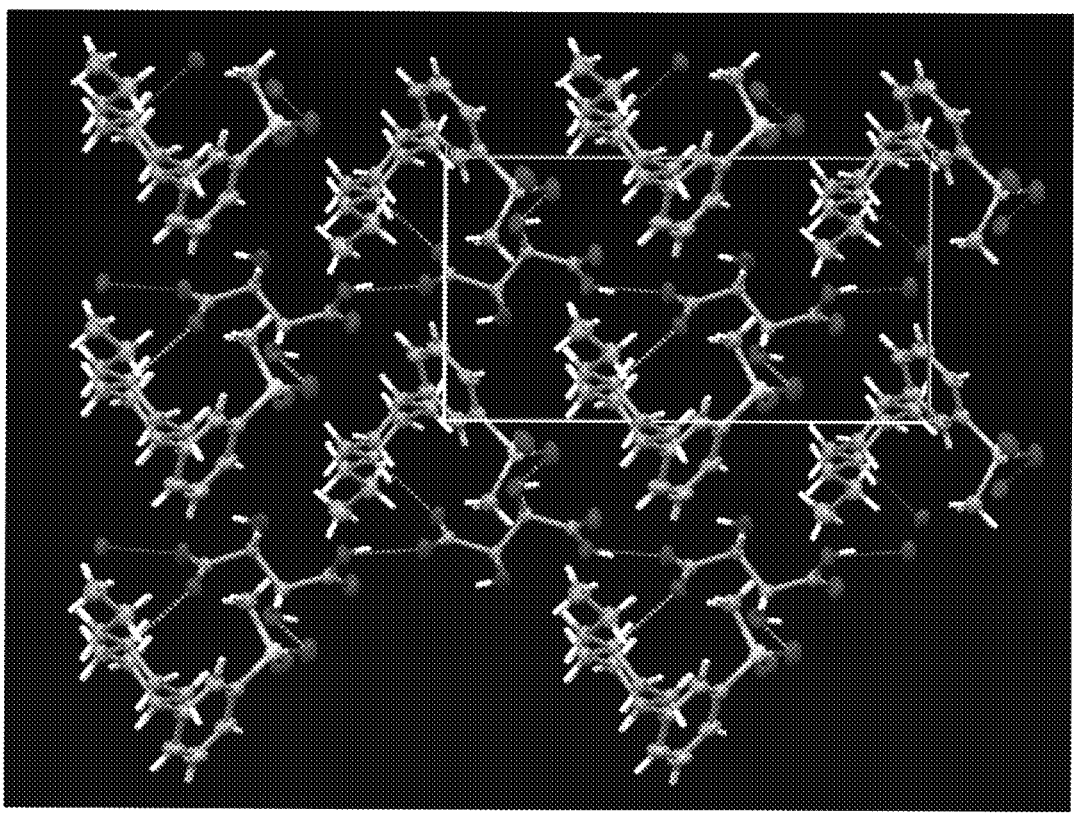

FIG. 9: The packing of pridopidine L-tartrate.

DETAILED DESCRIPTION OF THE INVENTION

The subject invention provides pridopidine L-tartrate.

Figure 2:
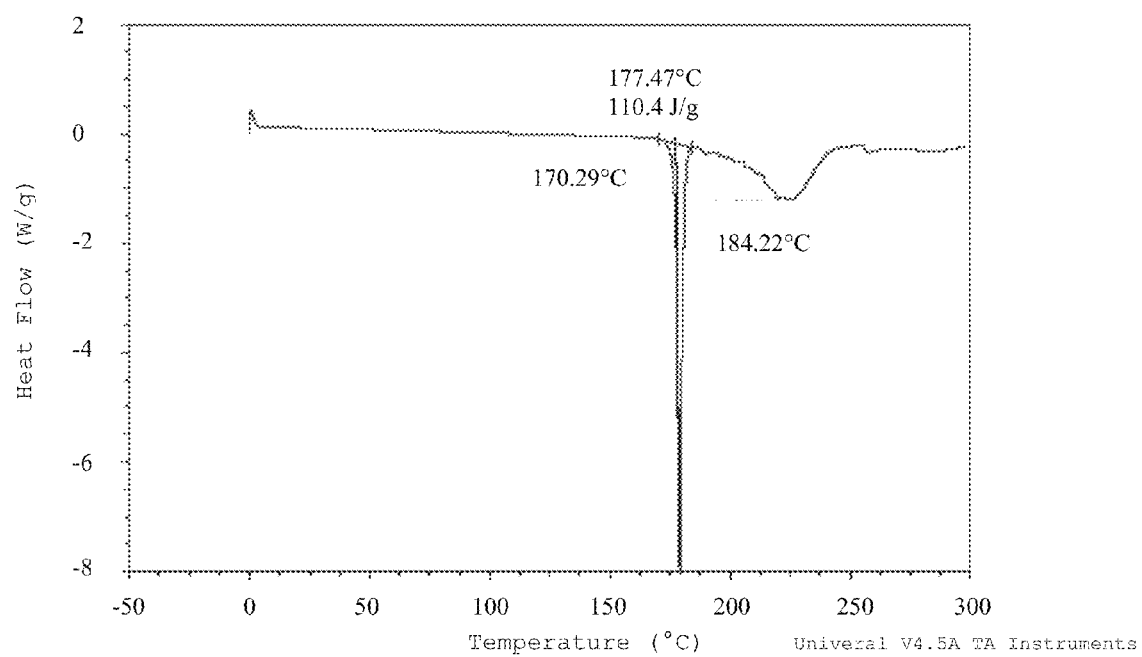
FIG. 2: DSC for pridopidine mono L-tartrate Form A1

In one embodiment, the pridopidine L-tartrate is pridopidine mono L-tartrate. In another embodiment, the pridopidine L-tartrate is isolated, In an embodiment, pridopidine L-tartrate is characterized by a DSC thermogram as shown in FIG. 2. In another embodiment, pridopidine L-tartrate is characterized by a XRPD pattern with characteristic peaks at 10.4°, 14.4°, 15.6°, 18.6°, 19.5°, 20.7°, 20.8°, 21.7°, 22.7°, 22.9°, 23.3°, 24.0°, and 28.1° 2 theta±0.2° 2 theta. In another embodiment, pridopidine L-tartrate is characterized by a XRPD pattern with characteristic peaks at 10.4°, 14.4°, 15.5°, 18.6°, 20.7°, 2.0.8°, and 24.0° 2 theta±0.2° 2 theta. In another embodiment, pridopidine L-tartrate is characterized by a XRPD pattern with characteristic peaks at 10.4°, 15.5°, and 20.8° 2 theta±0.2° 2 theta. In another embodiment, pridopidine L-tartrate is characterized by a XRPD pattern with reflections corresponding to the d-spacing values 8.5, 4.8, 4.3, and 3.7±0.1. In another embodiment, pridopidine L-tartrate is characterized by a XRPD pattern with reflections corresponding to the d-spacing values 8.5, 6.2, 5.7, 4.8, 4.3, and 3.7±0.1. In another embodiment, pridopidine L-tartrate is characterized by a XRPD pattern with reflections corresponding to the d-spacing values 8.5, 6.2, 5.7, 4.8, 4.5, 4.3, 4.1, 3.9, 3.8, 3.7, and 3.2±0.1. In another embodiment, pridopidine L-tartrate is characterized by a XRPD pattern with reflections corresponding to the d-spacing values 8.5, 4.8, 4.3, and 3.7±0.1. In another embodiment, pridopidine L-tartrate is characterized by a XRPD pattern with reflections corresponding to the d-spacing values 8.5, 5.7, and 4.3.

Figure 1:
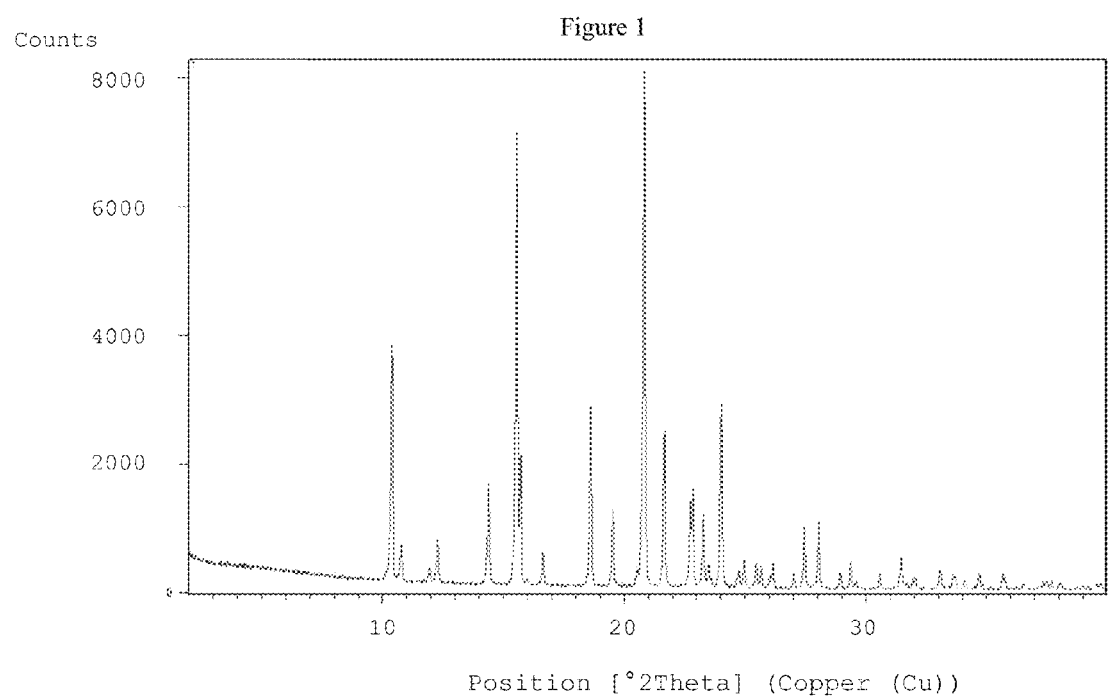
FIG. 1: XRPD for pridopidine mono L-tartrate Form A1. Pridopidine mono L-tartrate, Form A1 is also referred to as pridopidine L-tartrate hereafter.
Figure 3:
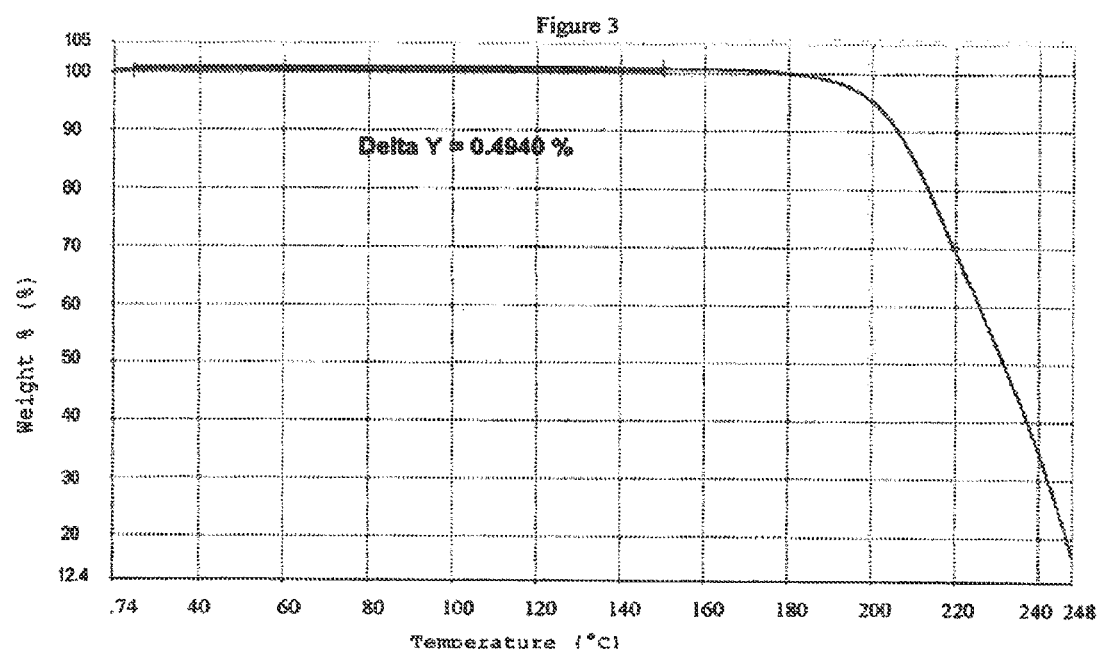
FIG. 3: TGA for pridopidine mono L-tartrate Form A1
Figure 4:
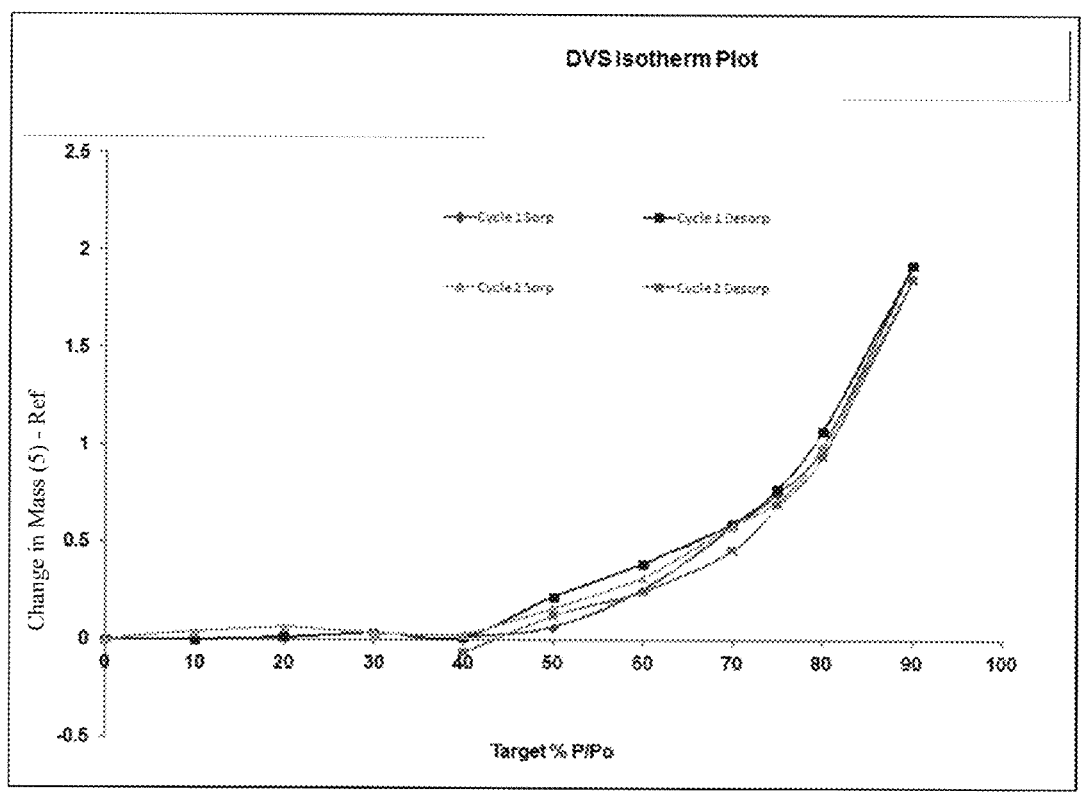
FIG. 4: DVS Isotherm for pridopidine mono L-tartrate Form A1
Figure 5:
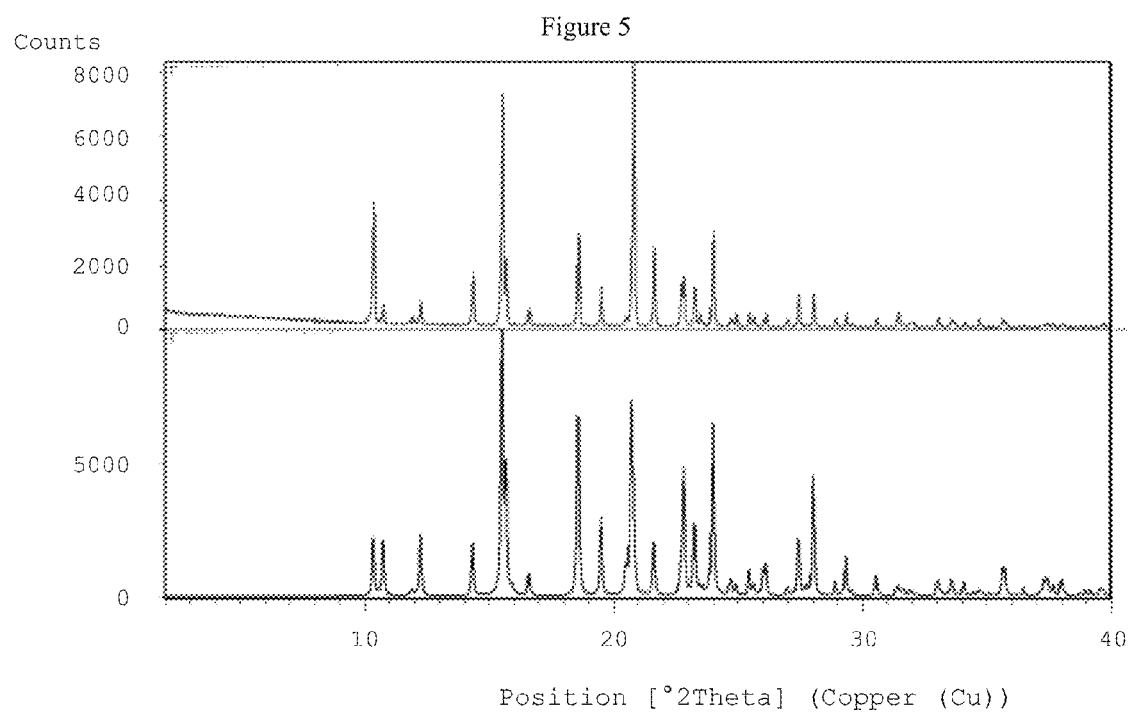
FIG. 5: Calculated (bottom) and Observed (top) XPRD Patterns of pridopidine L-tartrate
Figure 6A:
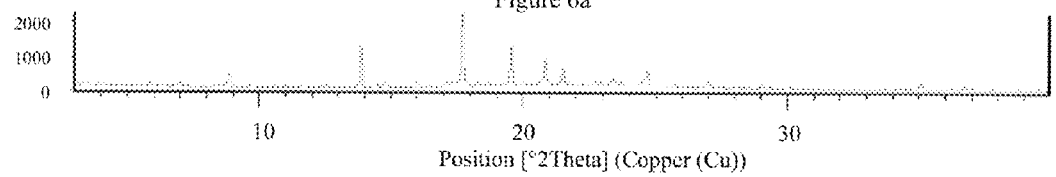
FIG. 6: XTYD data for various pridopidine salts as indicated below.
Figure 6B:
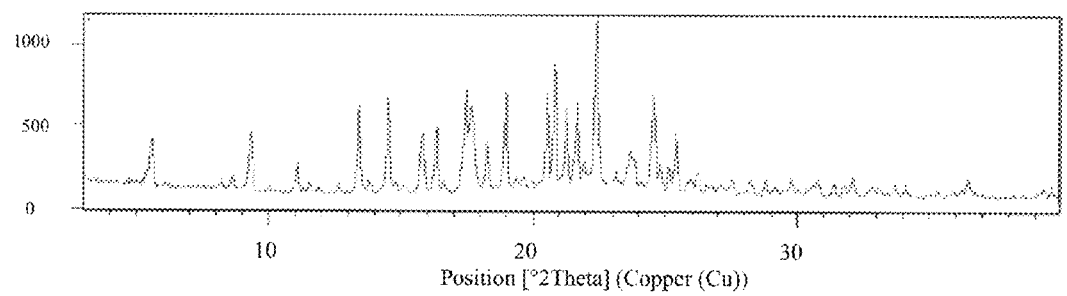
Figure 6C:
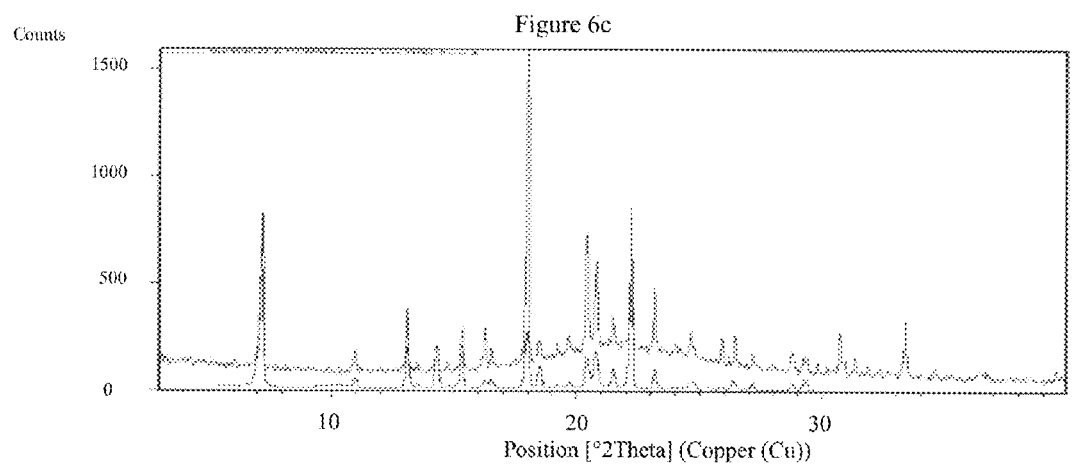
Figure 6G:
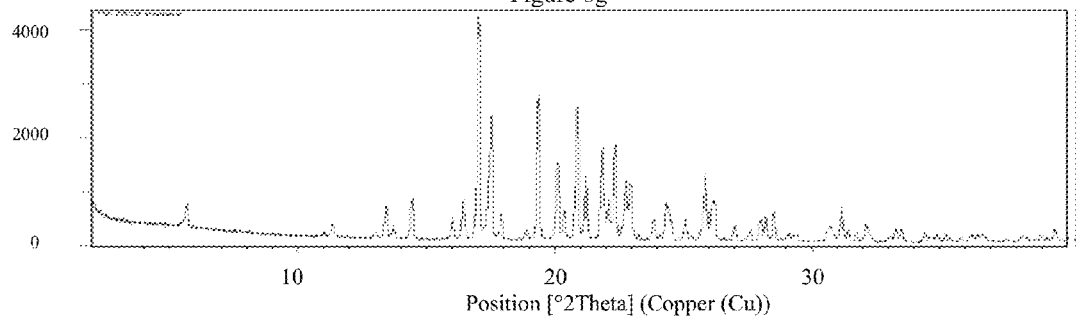
Figure 6H:
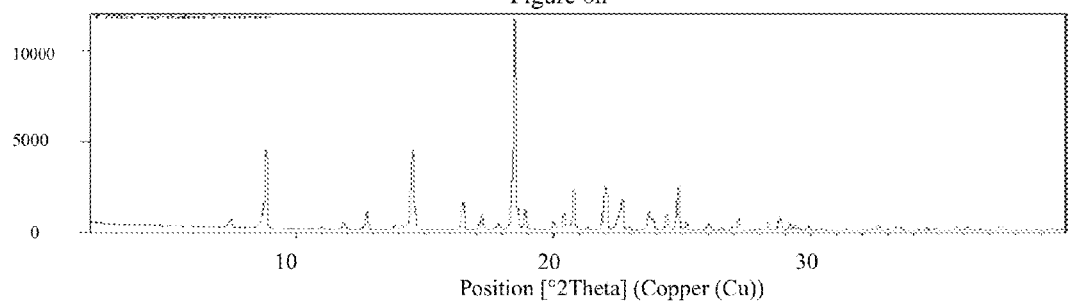
Figure 6I:
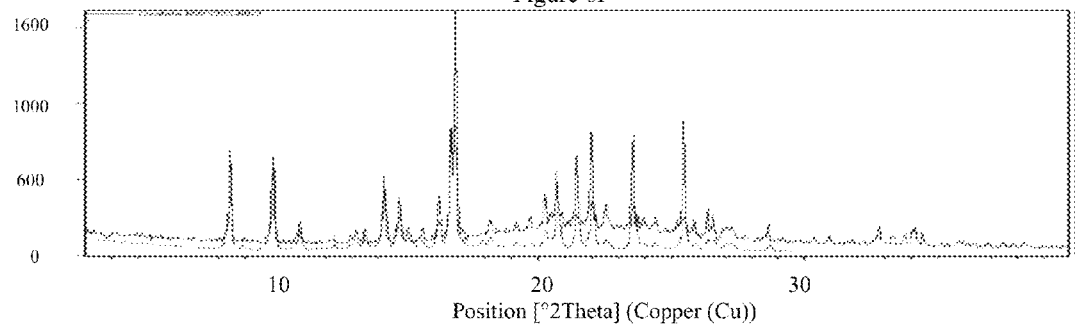
Figure 6J:
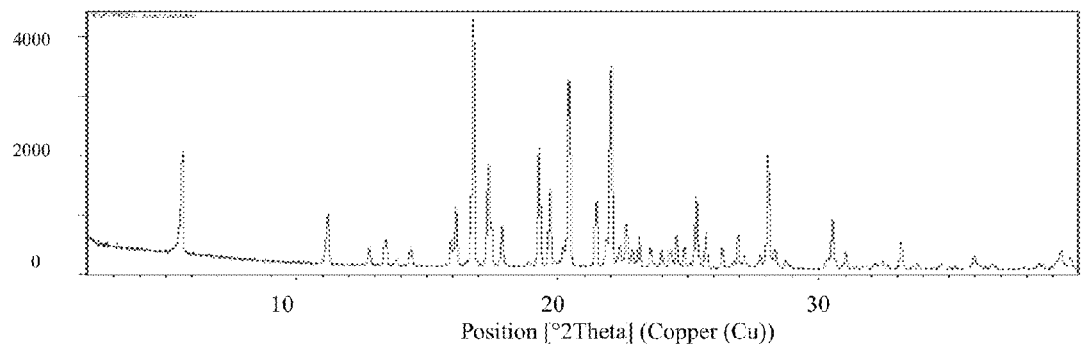
Figure 6K:
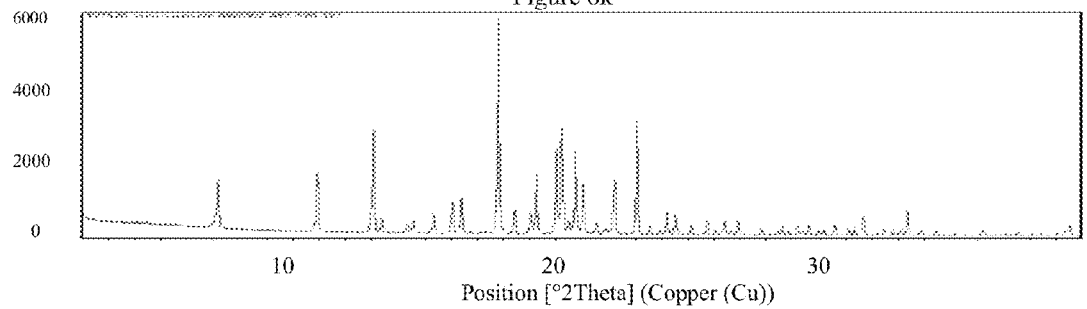
Figure 6L:
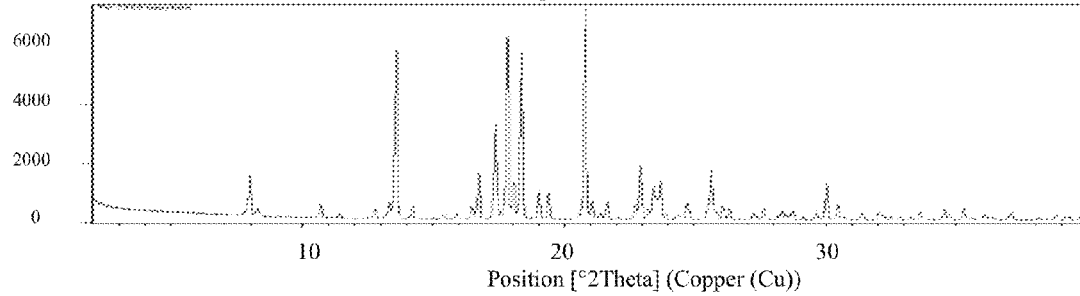

In an embodiment, pridopidine L-tartrate is characterized by a XRPD pattern as shown in FIG. 1. In another embodiment, pridopidine L-tartrate is characterized by having an endotherm with an onset of 178° C. and a peak max at 179° C. In another embodiment, pridopidine L-tartrate is characterized by having a TGA thermogram which shows a weight loss of about 0.03% to about 0.5% from 25° C. to 150° C. In another embodiment, pridopidine L-tartrate is characterized by having a TGA thermogram as shown in FIG. 3. In another embodiment, pridopidine L-tartrate is characterized by having a dynamic vapour sorption (DVS) profile which shows a weight gain of 0.02% at 40% Relative Humidity (RH); 0.73% at 70% RH, and/or 1.98% at 90% RH. In another embodiment, pridopidine L-tartrate is characterized by having a dynamic vapour sorption (DVS) profile as shown in FIG. 4.

In an embodiment, the pharmaceutical composition is together with one or more adjuvants, excipients, carriers and/or diluents. In another embodiment, the pharmaceutical composition is in the form of a capsule, a tablet or a liquid suspension. In another embodiment, the pharmaceutical composition is in the form of an oral dosage form.

In an embodiment the oral dosage unit form comprises between 22.5-315 mg pridopidine. In another embodiment, the oral dosage unit form comprises between 45-250 mg pridopidine. In another embodiment, the oral dosage unit form comprises between 45-135 mg pridopidine. In another embodiment, the oral dosage unit form comprises between 90-315 mg pridopidine. In another embodiment, the oral dosage unit form comprises about 22.5 mg pridopidine. In another embodiment, the oral dosage unit form comprises about 45 mg pridopidine. In another embodiment, the oral dosage unit form comprises about 67.5 mg pridopidine. In another embodiment, the oral dosage unit form comprises about 90 mg pridopidine. In another embodiment, the oral unit dosage form comprises about 100 mg pridopidine. In another embodiment, the oral dosage unit form comprises about 112.5 mg pridopidine. In another embodiment, the oral dosage unit form comprises about 125 mg pridopidine. In another embodiment, the oral dosage unit form comprises about 135 mg pridopidine. In another embodiment, the oral dosage unit form comprises about 150 mg pridopidine. In another embodiment, the oral dosage unit form comprises about 180 mg pridopidine. In another embodiment, the oral dosage unit form comprises about 200 mg pridopidine. In another embodiment, the oral dosage unit form comprises about 250 mg pridopidine. In another embodiment, the oral dosage unit form comprises about 315 mg pridopidine.

The subject invention also provides a composition comprising the pridopidine L-tartrate and a carrier. In an embodiment, the composition is free of L-tartaric acid. In another embodiment, the composition has less than 5% L-tartaric acid by weight, preferably less than 1% L-tartaric acid by weight, more preferably less than 0.1% L-tartaric acid by weight. In another embodiment, the composition further comprises pridopidine base. In an embodiment, the pridopidine base is present in an amount of less than 5% based on total pridopidine content of the composition.

In one embodiment, the composition is free of pridopidine base. In another embodiment, the composition has less than 5% pridopidine base by weight, preferably less than 1% pridopidine base by weight, more preferably less than 0.1% pridopidine base by weight.

In another embodiment, the composition is a pharmaceutical composition and the carrier is a pharmaceutically acceptable carrier. In one embodiment, the pharmaceutical composition of is in tablet form. In an embodiment, the tablet unit form comprises between 22.5-315 mg pridopidine. In another embodiment, the tablet unit form comprises between 90-315 mg pridopidine. In another embodiment, the tablet unit form comprises about 22.5 mg, about 45 mg, about 67.5, mg, about 90 mg, about 100 mg, about 112.5 mg, about 125 mg, about 135 mg, about 150 mg, about 180 mg, about 200 mg, about 250 mg, or about 315 mg pridopidine. In a further embodiment, the tablet unit form is prepared for once daily administration. In another embodiment, the tablet unit form is prepared for more than once daily administration.

The subject invention also provides a process for manufacture of pridopidine L-tartrate comprising:
    combining L-tartaric acid with pridopidine free base to form a mixture
    d) obtaining pridopidine L-tartrate from the mixture.

In one embodiment, the pridopidine free base or the L-tartrate acid is mixed with a solvent prior to or during step a. In another embodiment, the solvent is selected from one or more of ACN, EtOH, EtOAc, iPrOAc, MTBE, iPrOH, THF, and toluene. In a hither embodiment, the solvent is iPrOAc. The subject invention also provides priclopidine L-tartrate prepared by the process.

The subject invention also provides a method of treating a human subject afflicted with Huntington's disease comprising administering to the human subject an amount of the pridopidine L-tartrate, the composition or the pharmaceutical composition effective to treat the human subject.

The subject invention also provides the use of the pridopidine L-tartrate or the composition for the manufacture of a medicament for treating a subject afflicted Huntington's disease.

The subject invention also provides pridopidine besylate Form A1.

The subject invention also provides pridopidine besylate Form B1.

The subject invention also provides pridopidine fumarate, Form A1.

The subject invention also provides pridopidine fumarate, Form B1.

The subject invention also provides pridopidine fumarate, Form C1.

The subject invention also provides pridopidine genustate.

The subject invention also provides pridopidine glycolate.

The subject invention also provides pridopidine L-malate.

The subject invention also provides pridopidine napthalene 2-sulfonate.

The subject invention also provides pridopidine oxalate.

The subject invention also provides pridopidine succinate.

The subject invention also provides pridopidine succinate (hemi).

The subject invention also provides pridopidine tosylate.

Each embodiment disclosed herein is contemplated as being applicable to each of the other disclosed embodiments. Thus, all combinations of the various elements described herein are within the scope of the invention.

For example, the elements recited in the packaging and pharmaceutical composition embodiments can be used in the method and use embodiments described herein.

Terms

As used herein, and unless stated otherwise, each of the following terms shall have the definition set forth below.

As used herein, "effective" as in an amount effective to achieve an end means the quantity of a component that is sufficient to yield an indicated therapeutic response without undue adverse side effects (such as toxicity, irritation, or allergic response) commensurate with a reasonable benefit/risk ratio when used in the manner of this disclosure. For example, an amount effective to treat a movement disorder. The specific effective amount varies with such factors as the particular condition being treated, the physical condition of the patient, the type of mammal being treated, the duration of the treatment, the nature of concurrent therapy (if any), and the specific formulations employed and the structure of the compounds or its derivatives.

As used herein, an amount of pridopidine as measured in milligrams refers to the milligrams of pridopidine (4-[3-(methylsulfonyl)phenyl]-1-propyl-piperidine) present in a preparation, regardless of the form of the preparation. For example, a unit dose containing "90 mg pridopidine" means the amount of pridopidine in a preparation is 90 mg, regardless of the form of the preparation. Thus, when in the form of a salt, e.g. pridopidine L-tartrate, the weight of the salt form necessary to provide a dose of 90 mg pridopidine would be greater than 90 mg due to the presence of the salt.

As used herein, "about" in the context of a numerical value or range means±10% of the numerical value or range recited.

As used herein, to "treat" or "treating" encompasses, e.g., reducing a symptom, inducing inhibition, regression, or stasis of the disorder and/or disease. As used herein, "inhibition" of disease progression or disease complication in a subject means preventing or reducing the disease progression and/or disease complication in the subject.

By any range disclosed herein, it is meant that all hundredth, tenth and integer unit amounts within the range are specifically disclosed as part of the invention. Thus, for example, 0.01 mg to 50 mg means that 0.02, 0.03 . . . 0.09; 0.1, 0.2 . . . 0.9; and 1, 2 . . . 49 mg unit amounts are included as embodiments of this invention.

A characteristic of a compound refers to any quality that a compound exhibits, e.g., peaks or retention times, as determined for example by 1H nuclear magnetic spectroscopy, 13C nuclear magnetic spectroscopy, mass spectroscopy, infrared, ultraviolet or fluorescence spectrophotometry, gas chromatography, thin layer chromatography, high performance liquid chromatography (HPLC), elemental analysis, Ames test, dissolution, stability and any other quality that can be determined by an analytical method. Once the characteristics of a compound are known, the information can be used to, for example, screen or test for the presence of the compound in a sample. Quantity or weight percentage of a compound present in a sample can be determined by a suitable apparatus, for example, a HPLC.

As used herein, an "isolated" compound is a compound isolated from the crude reaction mixture following an affirmative act of isolation. The act of isolation necessarily involves separating the compound from the other known components of the crude reaction mixture, with some impurities, unknown side products and residual amounts of the other known components of the crude reaction mixture permitted to remain. Purification is an example of an affirmative act of isolation.

As used herein, a composition that is "free" of a chemical entity means that the composition contains, if at all, an amount of the chemical entity which cannot be avoided. In another embodiment, a composition that is free of a chemical entity contains less than 5% of the chemical entitiy, by weight. In a further embodiment, a composition that is free of a chemical entitiy contains less than 1% of the chemical entity, by weight. In another embodiment, a composition that is free of a chemical entitiy contains less than 0.5% of the chemical entity, by weight. In an additional embodiment, a composition that is free of a chemical entitiy contains less than 0.1% of the chemical entity, by weight. In a further embodiment, a composition that is free of a chemical entitiy contains 0.0% of the chemical entity, by weight.

Pridopidine L-tartrate refers to pridopidine mono L-tartrate unless otherwise specificed.

Pridopidine hydrochloride refers to Form A1 unless otherwise specificed.

When a series of values (for example d-spacing values) are given and following by a plus minus symbol and a number, such as d-spacing values 8.5, 5.7, and 4.3±0.1, this means that each and every value preceeding the ±0.1 may be up to 0.1 more or 0.1 less than the value. For example "d-spacing values 8.5, 5.7, and 4.3±0.1" means a d-space value from 8.4 through 8.6, a d-space value from 5.6 through 5.8, and a d-space value from 4.2 through 4.4.

In this application, all d-spacing values are given in units of angstroms (A), regardless of whether a unit is specified or not.

Pharmaceutical Compositions

While the compounds for use according to the invention may be administered in the form of the raw compound, it is preferred to introduce the active ingredients, optionally in the form of physiologically acceptable salts, in a pharmaceutical composition together with one or more adjuvants, excipients, carriers, buffers, diluents, and/or other customary pharmaceutical auxiliaries.

In an embodiment, the invention provides pharmaceutical compositions comprising the active compounds or pharmaceutically acceptable salts or derivatives thereof, together with one or more pharmaceutically acceptable carriers therefore, and, optionally, other therapeutic and/or prophylactic ingredients know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy, exemplified by oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by the skilled person by use of standard methods and conventional techniques appropriate to the desired formulation. When desired, compositions adapted to give sustained release of the active ingredient may be employed.

Further details on techniques for formulation and administration may be found in the latest edition of Remington's Pharmaceutical Sciences (Maack Publishing Co., Easton, Pa.).

This invention will be better understood by reference to the Experimental Details which follow, but those skilled in the art will readily appreciate that the specific experiments detailed are only illustrative of the invention as described more fully in the claims which follow thereafter.

Experimental Details

EXAMPLES

Background to Examples

Pridopidine is currently being developed for treatment of Huntington's disease. It is a competitive antagonist of dopamine D2 receptors that increases the release and metabolism of dopamine in the subcortical area. In addition, it increases the release and turnover of dopamine and norepinephrine in cortical areas.

The solvents used for the following examples were: acetone; acetonitrile (ACN); ethanol (EtOH); ethyl acetate (EtOAc); isopropyl acetate (iPrOAc); methanol (MeOH); methyl tert-butyl ether (MTBE); 2-propanol (iPrOH); tetrahydrofuran (THF); toluene; dichloromethane (DCM); and chloroform. The solvents had a high purity (purity ≥99%).

List of Equipment and Procedures:

XRPD—X-Ray Powder Diffraction: Powder XRD patterns were recorded on a PANalytical X'Pert Pro diffractometer equipped with an X'celerator detector using Cu Kα radiation at 45 kV and 40 mA. The diffractometer was controlled with PANalytical Data Collector2. All samples were analyzed using algorithms in HighScorePlus.

DSC—Differential Scanning Calorimetry: Thermal curves were acquired using a TA Discovery DSC unit. Solid samples of 5-20 mg were weighed into Tzero™ aluminum pinhole hermetically sealed pin hole pans. The DSC cell was then purged with nitrogen and the temperature heated at 10° C./min from 0 to 300° C. Indium (Tm=156.6° C.; ΔHFus=28.45 J g−1) was used for calibration.

TGA—Thermogravimetric Analysis: Thermal curves were acquired using a Perkin-Elmer Pyris 1 TGA unit running Pyris software version 6.0 calibrated with alumel (95% nickel, 2% manganese, 2% aluminum and 1% silicon), nickel and calcium oxalate Lot P11105-039-J. TGA samples between 1-5 mg were monitored for percent weight loss as heated from 25 to 250° C. at 10° C./Erin in a furnace purged with Helium at ca. 50 mL/min.

DVS—Measurement of Dynamic Vapor Sorption: DVS experiments have been carried out using the DVS-HT instrument (Surface Measurement Systems, London, UK). This instrument measures the uptake and loss of vapor gravimetrically using a recording ultra-microbalance with a mass resolution of ±0.1 μg. The vapor partial pressure (±1.0%) around the sample is controlled by mixing saturated and dry carrier gas streams using electronic mass flow controllers. The desired temperature is maintained at ±0.1° C. The samples (1-10 mg) were placed into the DVSI-fT or DVS-1 instruments at the desired temperature. The sample was loaded and unloaded at 40% RH and 25° C. (typical room conditions). A moisture sorption isotherm was performed as outlined below (2 scans giving 1 complete cycle). The software uses a least squares minimization procedure together with a model of the mass relaxation, to predict an asymptotic value. The measured mass equilibration value must be within 2% of that predicted by the software before proceeding to the next % RH value. The minimum equilibration time was set to 1 hour and the maximum to 4 hours.

NMR—Measurement of 1H-NMR Spectrum: The structure information (i.e., ratio of free base and acid and residue solvent) of the forms were determined by 1H-NMR spectroscopy using a Bruker DPX400 instrument running under conditions optimized to give the best available spectrum for each sample. Each sample (2-4 mg) was normally dissolved in 0.75 mL DMSO-d6 and spectrum obtained in thin walled glass tubes (4×14 mm).

Estimation of Water Solubility: A kinetic solubility experiment was performed. Powder samples were placed in glass vials and shaken for 20 minutes in water. The hydrochloride and L-tartrate pridopidine salt solutions were not saturated (i.e., no visible solid was present). The samples were then centrifuged to insure that no solids remained. The concentration of pridopidine in the supernatant was measured by HPLC and calculated based on a standard curve. Pridopidine free base equilibrium solubility was measured in water and at pH 7 in a sodium phosphate buffer (0.15 M ionic strength). Excess pridopidine was suspended in the solutions in glass vials and shaken for 72 hours at 25° C. The samples were then centrifuged and the pH of the supernatant was measured. The concentration of pridopdine in the supernatant was measured by HPLC and calculated based on a standard curve.

Example 1: Salts 0.14M (40 mg/mL) stock solutions of pridopidine free base in 2-propanol were prepared. 0.125M acid solutions were prepared using the acid quantities and solvents (20 mL) detailed in Table 1.

TABLE 1

| Acid | MW (mg/mmol) | Purity on receipt | Acid added (mg) | Sovent used |
|---|---|---|---|---|
| L-malic acid | 134.09 | — | 335 | Acetone |
| D, L-tartaric acid | 150.09 | 99.9% | 188 | Acetone |
| L-tartaric acid | 150.09 | 99.9% | 188 | Acetone |
| Naphthalene 2-sulfonic acid | 208.24 | 94% | 554 | EtOAc |
| Oxalic acid, dihydrate | 126.07 | — | 315 | EtOH |
| Succinic acid | 118.09 | ≥99% | 298 | iPrOH |
| Fumaric acid | 116.07 | 99% | 290 | MeOH |
| Gentist acid | 154.12 | 99% | 389 | MeOH |
| Glycolic acid | 76.06 | ≥98% | 190 | MeOH |
| Benzene sulfonic acid monohydrate | 158.18 | 98% | 404 | EtOAc |
| P-toluene sulfonic acid monohydrate | 190.22 | 97% | 490 | EtOAc |

| Acid | Class | $pK_a1$ | $pK_a2$ | — |
|---|---|---|---|---|
| L-malic acid | 1 | 3.46 | — | — |
| D, L-tartaric acid | 1 | 3.02 | 4.36 | — |
| L-tartaric acid | 1 | 3.02 | 4.36 | — |
| Naphthalene 2-sulfonic acid | 2 | 0.17 | | — |
| Oxalic acid, dihydrate | 2 | 1.27 | | — |
| Succinic acid | 1 | 4.21 | 5.64 | — |
| Fumaric acid | 1 | 3.03 | 4.38 | — |
| Gentist acid | 2 | 2.93 | | — |
| Glycolic acid | 1 | 3.28 | | — |
| Benzene sulfonic acid | 2 | 0.70 | | — |
| p-Toluene sulfonic acid | 2 | −1.34 | | — |

Approximately 500 μL of the pridopidine free base stock solution (i.e., ~20 mg or 0.07 mmol of free base) were added to a 4 mL glass vial, along with approximately 630 μL of 0.125M acid solution (i.e., 1.1 equivalents of the acid). The solvents were allowed to evaporate in uncovered vials in the hood.

When no solvent remained, the vial was placed in a vacuum oven (approximately 60° C., house vacuum) to dry overnight. Approximately 200 μL of solvent were added to the dried mixture. The vials were stirred at room temperature for at least 24 hours. Twelve solvents were evaluated. They were acetone, ACN, EtOH, EtOAc, iPrOAc, MeOH, MTBE, iPrOH, THF, toluene, DCM, and chloroform. After stirring, several vials had gone to dryness due to the evaporation of the solvent. In the vials where solid and liquid remained, the solvent in the mixture was allowed to evaporate to yield solids. The solids were evaluated by XRPD. In the cases where no solids were obtained, the solvents were evaporated to dryness in a vacuum oven (approximately 60° C. and house vacuum) for more than 24 hours. The recovered solids which were clear films in the vials were treated with ~200 μL of solvent mixtures. Water miscible solvents were mixed with 10% water and water immiscible solvents with 10% heptanes. The mixtures were stirred at room temperature for more than 24 hours.

Pridopidine and L-tartaric acid: Slurries were obtained from ACN, EtOH, EtOAc, iPrOAc, MTBE, iPrOH, THF, and toluene. These slurries were filtered, and the resulting solids were dried and analyzed by XRPD. All solids were crystalline with the same XRPD pattern (FIG. 1), which was different from those of free base and L-tartaric acid. Proton NMR on one of the sample confirmed the solids to be a pridopidine mono L-tartrate.

Pridopidine and D, L-tartaric acid: Slurries were formed from all solvents except MeOH. The slurries from acetone and EtOH were filtered and the resulting solids were dried and analyzed by XRPD. Pridopidine D,L-tartrate was formed. All solids were crystalline with the same XRPD pattern consistent with that of pridopidine L-tartrate (FIG. 1).

Pridopidine and L-malic acid: Slurry was only obtained from isopropyl acetate. This slurry was filtered, and the obtained solids were dried and analyzed by XRPD. The solids were crystalline and had a XRPD pattern which was different from those of free base and L-malic acid. NMR test confirmed the solids to be a pridopidine mono L-malate. A seeding step is recommended because formation of pridopidine malate is difficult and may fail when no seeds are added. Pridopidine Mono L-malate Form A1 was also made by adding ~200 mg of pridopidine free base and ~10 mL of iPrOAc to a 20 mL vial and then stirring the mixture. Next, ~105 mg of L-malic acid and ~5 mL of iPrOAc was added to a 4 mL vial and heated to obtain clear solution. This solution was then added, drop-wise, to the one with pridopidine free base and 2-5 mg of pridopidine malate was added as seeds. The solution was stirred at room temperature for at least 24 h and then filtered to obtain solids. The solids were dried in a vacuum oven at ~60° C. overnight.

Pridopidine and benzene sulfonic acid: Slurries formed from EtOAc, iPrOAc, EtOH, MTBE, iPrOH, THF, and toluene. The toluene slurry formed pridopidine besylate Form A1, as determined by XRPD patterns. The process was repeated using THF and toluene as solvents, and pridopidine besylate Form B1 was formed as determined by XRPD patterns. Solids from THF appeared to be extremely hygroscopic and began to deliquesce during vacuum filtration using a Buchner funnel, presumably caused by a small amount of water from atmosphere. Pressure filtration is recommended if THF is used as the salt forming solvent. Pridopidine besylate B1 was also made by charging about 80 mg of pridopidine free base, about 48 mg benzene sulfonic acid, and about 0.8 mL of THF to a vial. Next, the resulting solution was stirred at room temperature for at least 48 h and filtered to obtain solids (pressure filtration is recommended). The solids were dried in a vacuum oven at about 60° C. overnight.

Pridopidine and Fumaric acid: Slurries were obtained from EtOH, iPrOAc, and MTBE. They were filtered, and the isolated solids were dried and analyzed by XRPD. The solids from MTBE and iPrOAc displayed a similar XRPD pattern and were assigned as pridopidine fumarate Form B1. The solids from EtOH displayed another pattern, denoted as pridopidine fumarate Form C1. The procedure was repeated on larger scale with MTBE and ethanol as solvents. The solids from MTBE were a mixture of pridopidine fumarate Forms B1 and C1. The XRPD pattern of solids from EtOH were were determined to be pridopidine fumarate Form A1. Pridopidine mono fumarate, Form A1 was also made by charging about 40 mg of pridopidine free base, about 18.2 mg of fumaric acid, and ~0.5 mL of ethanol to a vial then heating the solution to ~40° C.-50° C. to obtain a clear solution. Next the resulting solution is stirred at room temperature overnight. The resulting slurry is filtered to obtain solids which are dried in a vacuum oven at ~60° C. overnight. Pridopidine mono fumarate, Form B1 is also made by charging ~20 mg of pridopidine free base, ~630 μL of 0.125M fumaric acid in MeOH to a vial. The mixture is then air-dried and then dried in a vacuum oven at ~50° C. and house vacuum. Next, ~200 μL of MTBE is added to the dried mixture and the resulting solution is stirred at temperature (~22-24° C.) for at least 24 h. The resulting slurry is filtered to obtain solids and the solids are dried in a vacuum oven at ~60° C. overnight. Pridopidine mono fumarate, Form C1 is also made by charging ~40 mg of pridopidine free base, ~18.2 mg of fumaric acid, and ~0.5 mL of MTBE to a vial. The resulting solution is stirred at room temperature overnight then filtered to obtain solids. The solids are dried in a vacuum oven at ~60° C. overnight.

Pridopidine and Dentist acid: Slurries were obtained from iPrOH, iPrOAc, and EtOAc. The slurries from iPrOH and iPrOAc were filtered and the resulting solids were dried and analyzed by XRPD. All solids were crystalline with the same XRPD pattern. NMR confirmed the solids to be pridopidine mono gentistate. Pridopidine mono gentistate was also made by charging ~80 mg of pridopidine free base and ~0.8 mL of iPrOH to a vial then sonicating for 1 to 2 minutes to obtain a clear solution. ~49 mg of gentistic acid was added and a slurry formed. The slurry was stirred at room temperature overnight then filtered to obtain solids which were dried in a vacuum oven at ~60° C. overnight.

Pridopidine and Glycolic acid: A slurry was only obtained from MTBE. The slurry was filtered and the obtained solids were dried and then analyzed by XRPD. The solids were crystalline and had a XRPD pattern different those of free base and glycolic acid. NMR confirmed the solids to be a pridopidine mono glycolate. Pridopidine mono glycolate was also made by adding ~80 mg of pridopidine free base, 22 mg of glycolic acid, and ~3.2 mL of MTBE to a vial. The mixture is then stirred at room temperature for at least 12 h then filtered to obtain solids (pressure filtration is recommended). The solids are dried in a vacuum oven at ~60° C. overnight.

Pridopidine and Naphthalene 2-sulfonic acid: Slurries were obtained from all the solvents. The slurry from ACN was filtered and the solids were dried and analyzed by XRPD. NMR on the sample confirmed the solids to be a pridopidine mono naphthalene 2-sulforiate. Pridopidine mono naphthalene 2-sulfonate was also made by charging ~80 mg of pridopidine free base and ~0.4 mL of acetonitrile to a vial then sonicating for 1 to 2 minutes to obtain a clear solution. ~70 mg of naphthalene 2-sulfonic acid, hydrate is added and the solution becomes clear, and then solids begin to form. The resulting slurry is stirred at room temperature overnight then filtered to obtain solids. The solids were dried in a vacuum oven at ~60° C. overnight.

Pridopidine and Oxalic acid, dehydrate: Slurries were obtained from all the solvents studied, except MeOH. The slurry of EtOH was filtered and the solids were dried and analyzed by XRPD. The solids were crystalline with an XRPD pattern corresponding to pridpidine oxalate. Pridopidine oxalate was also made by charging ~80 mg of pridopidine free base, 45 mg of oxalic acid (dehydrate), and ~0.8 mL of ethanol to a vial. The mixture was then stirred at room temperature for >12 h then filtered to obtain solids. The solids were dried in a vacuum oven at ~60° C. overnight.

Pridopidine and Succinic acid: Slurries were obtained from acetone, ACN, EtOAc, and MeOH. These slurries were filtered, and the resulting solids were dried and analyzed by XRPD. All solids were crystalline with the same XRPD pattern which was different from those of free base and succinic acid. NMR on one of the samples confirmed the solids to be pridopidine mono succinate. Pridopidine mono succinate was also made by stirring about 80 mg of pridopidine free base, about 0.8 mL of iPrOAc, and about 37 mg succinic acid in a vial at room temperature overnight, then pridopidine semi succinate, as confirmed by XRPD and NMR, was obtained from the resulting slurry. Pridopidine hemi succinate was made by charging ~80 mg of pridopidine free base and ~0.8 mL of iPrOAc to a vial then adding ~37 mg of succinic acid to obtain a mixture, which was stirred at room temperature overnight then filtered to obtain solids. The solids were dried in a vacuum oven at ~60° C. overnight.

Pridopidine and p-Toluene sulfonic acid, monohydrate: Slurries were obtained from all the solvents studied, except MeOH. These slurries were filtered and the resulting solids were dried and analyzed by XRPD. All solids were crystalline with the same XRPD pattern. NMR on one of the sample confirmed the solids to be pridopidine mono tosylate. Pridopidine mono tosylate was also made by charging ~80 mg of pridopidine free base and ~0.4 mL of acetone to a vial then sonicating for 1 to 2 minutes to obtain clear a solution. Next, ~61.3 mg of p-toluene sulfonic acid, monohydrate was added and the slurry was stirred at room temperature overnight and then filtered to obtain solids. The solids were dried in a vacuum oven at ~60° C. overnight.

Example 2: Procedure for Making Pridopidine Mono L-Tartrate Form A1

Add ~320 mg of pridopidine free base and ~3.2 mL of ACN to a 4 mL vial. Stir the mixture to obtain clear solution. Add ~200 mg of L-tartaric acid. Stir the mixture at room temperature. The solution becomes clear initially, and then thick slurry forms. Continue stirring for >12 h at room temperature. Filter the resulting slurry to obtain the solids. Dry the solids in a vacuum oven at approximately 60° C. overnight. Approximately 500 mg of solids pridopidine mono L-tartrate form A1 was obtained.

Example 3: Properties of the Various Pridopidine Salts

Pridopidine mono L-tartrate Form A1: Pridopidine mono L-tartrate Form A1 is an off white to white, crystalline solid with the XRPD pattern shown in FIG. 1. When subjected to DSC testing, it displayed an endotherm onset at 178° C. and a peak max at 179° C. (FIG. 2). It loses 0.5% weight when heated from 25° C. to 150° C. at a rate of 10° C./min (FIG. 3). The DVS test on the sample indicates a weight gain of 0.02% at 40% RH; 0.73% at 70% RH, and 1.98% at 90% RH. There is no change in XRPD pattern before and after the DVS test.

Pridopidine mono Besylate Form A1: When subjected to DSC testing, it displayed an endotherm onset at 141° C. and a peak max at 143° C. It loses 0.02% of weight when heated from 25° C. to 150° C. in a rate of 10° C./min.

Pridopidine mono besylate Form B1: When subjected to DSC testing, it displayed an endotherm onset at 146° C. and a peak max at 147° C. It loses 0.1% of weight when heated from 25° C. to 150° C. at a rate of 10° C./min. DVS test on the sample indicates weight gains of 0.2% at 40% RH; 0.6% at 70% RH, and 1.4% at 90% RH. The small (less than 0.2%) hysteresis in the DVS isotherm is likely caused by the bulk absorption.

Pridopidine fumarate Form A1: this form has a melting point of 186° C. When subjected DVS test, it has a weight gain of 0.6% at 40% RH, 0.8% at 75% RH and 3.6% at 90%.

Pridopidine mono fumarate Form B1: When subjected to DSC testing, it displayed melting points of 129° C. and 157° C. It loses 0.9% of weight when heated from 25° C. to 150° C. at a rate of 10° C./min. DVS testing on the sample indicates a weight gain of 0.3% at 40% RH; 0.5% at 70% RH, and 2.14% at 90% RH. There is no change of XRPD pattern before and after the DVS test.

Pridopidine mono fumarate Form C1: When subjected to DSC test (i.e., 25° C. to 150° C. with ramping rate of 10° C./min), it displayed an endotherm onset at 155° C. and a peak max at 157° C. It loses 0.9% of weight when heated from 25° C. to 150° C. in a rate of 10° C./. DVS testing was performed on a mixture of Form B1 and Form C1. The XRPD pattern before and after the DVS test showed a change from a mixture to Form C1. Since the sample had converted to Form C1 at the end of the experiment, the water uptake shown should be a good indicator of that of Form C1. The DVS test shows a weight gain of 0.02% at 40% RH; 0.04% at 70% RH, and 0.14% at 90% RH.

Pridopidine mono gentistate Form A1: When subjected to DSC test (0° C. to 300° C. with ramping rate of 10° C./min), it displayed an endotherm onset at 85° C. and a peak max at 96° C. It loses 0.1% weight when heated from 25° C. to 150° C. in a rate of 10° C./min. A DVS experiment indicates a weight gain of 0.1% at 40% RH, 2.7% at 70% RH, and 8.0% at 90% RH. There is no change in XlZPD pattern before and after the DVS test.

Pridopidine mono glycolate Form A1: When subjected to DSC testing, it displayed an endotherm onset at 85° C. and a peak max at 95° C. It loses 1.3% weight when heated from 25° C. to 150° C. at a rate of 10° C./min. It is very hygroscopic. A DVS run shows a weight gain of 8% at 40% RH, 30% at 70% RH, and 59% at 90% RH. Deliquescence occurred.

Pridpidine mono naphthalene 2-sulfonate Form A1: When subjected to DSC testing, it displayed an endotherm onset at 166° C. and a peak max at 158° C. It loses 0.1% weight when heated from 25° C. to 150° C. in a rate of 10° C./min. The DVS test on the sample indicates an average weight gain of water gain 0.2% at 40% RH, 1.2% at 70% RH; and 2.7% at 90% RH. There is no change in XRPD pattern before and after the DVS test.

Pridopidine mono oxalate Form A1: It loses 0.7% of weight when heated from 25° C. to 150° C., has an endotherm onset at 140.9° C. and a peak max at 141.9° C., and takes up water, 0.4% at 0% RH, 1.0% at 70% RH, and 1.7% at 90% RH. The DSC thermogram of this sample displays only one endotherm at 142° C. It loses 0.4% weight when heated from 25° C. to 150° C. in a rate of 10° C./min. Consistent with this DSC result, VT-XRPD performed on the sample shows amorphous material after the melt at 148° C. There is no indication of recrystallization.

Pridopidine mono succinate Form A1: When subjected to DSC testing, it displayed melting points of 63° C. and 91° C. It loses 1.4% weight when heated from 25° C. to 150° C. at a rate of 10° C./min. The salt is very hygroscopic. The DVS test on the sample indicates an average weight gain of 1% at 40% RH; 15% at 70% RH, and 36% at 90% RH. The sample deliquesced during the DVS test.

Pridopidine hemi succinate Form A0.5: When subjected to DSC testing, it displayed a melting point of 102° C. with some minor endothermic event at 58° C., 73° C., and 88° C. it loses 0.8% weight when heated from 25° C. to 150° C. at a rate of 10° C./min. DVS testing on the sample indicates an average weight gain of 3% at 40% RH; 4% at 70% RH, and 37% at 90% RH. The sample deliquesced during the DVS test.

Pridopidine mono tosylate Form A1: It loses 0.1% weight when heated from 25° C. to 150° C. at a rate of 10° C./min. When subjected to DSC testing, it displayed an endotherm onset at 168° C. and a peak max at 169° C. The DVS test on the sample indicates a weight gain of 0.02% at 40% RH; 0.1% at 70% RH, and 0.2% at 90% RH. There is no change in XRPD pattern before and after the DVS test.

Example 4: Water Solubility

Water solubility was evaluated for hydrochloride (form A1), L-tartrate, and L-malate. The kinetic water solubility was measured after the samples (i.e., salt and water) were shaken for 20 minutes. At this point the hydrochloride and the L-tartrate solutions were clear. The results are as following:

TABLE 2

Water Solubility of select forms of pridopidine

|  | Conc. | pH |
| --- | --- | --- |
| Hydrochloride | >230 mg/mL | 6.0 |
| L-tartrate | >65 mg/mL | 3.3 |
| L-malate | 76 mg/mL | 3.9 |

The salt forms studied here displayed reasonable water solubility and are considered, in terms of solubility, acceptable.

Conclusions:

Pridopidine mono L-tartrate, Form A1, displays acceptable melting point, hygroscopicity, solubility and polymorphism. The acid is in the same safety class as the pridopidine hydrochloride. The mono L-tartrate has high water solubility (i.e., >65 mg/mL).

Discussion and Conclusion of Examples 1-4

The properties of these salts of pridopidine are detailed in Table 3 below.

TABLE 3

| Form[a] | Melting point (° C.) | TGA weight loss | Hygroscopicity 40% RH | Hygroscopicity 75% RH | Hygroscopicity 90% RH | Identified Polymorphs | Class |
| --- | --- | --- | --- | --- | --- | --- | --- |
| HCl (A or Form I) | 203 | 0.60% | 0.1% | 0.45% | 7.3% | 2 | 1 |
| HCl (B or Form II) | 210 | NM | NM | NM | NM |  |  |
| HBr | 197 | NM | 0.04% | 0.08% | 0.12% | 1 | 3 |
| L-tartrate | 179 | 0.49% | 0.02% | 0.7% | 2.0% | 1 | 1 |
| Besylate, Form A1 | 142 | NM | NM | NM | NM | 2 | 2 |
| Besylate, Form B1 | 145 | 0.12 | 0.2 | 0.6 | 1.4 |  |  |
| Fumarate, Form A1 | 186 | NM | 0.6 | 0.8 | 3.6 | 3 | 1 |
| Fumarate, Form B1 | 157 | 0.93 | 0.3 | 0.5 | 2.5 |  |  |
| Fumarate, Form C1 | 156 | 0.9 | 0.02 | 0.04 | 0.14 |  |  |
| Gentistate | 96 | 0.12 | 0.08 | 2.7 | 8.0 | 1 | 2 |
| Glycolate | 95 | 1.31 | 1.1 | 29.5 | 58.5 | 1 | 1 |
| L-malate | 117 | 0.17% | 0.1% | 0.2% | 17.2% | 1 | 1 |
| Napthalene 2-sulfonate | 168 | 0.10 | 0.03 | 1.3 | 2.7 | 1 | 2 |
| Oxalate | 140 | 0.69 | 0.4 | 1.0 | 1.7 | 1 | 2 |
| Succinate | 91 | 1.4 | 0.01 | 12 | 36 | 1 | 1 |
| Succinate (hemi) | 102 | 0.8 | 3 | 40 | 70 | 1 | 1 |
| Tosylate | 169 | 0.20 | 0.02 | 0.1 | 0.2 | 1 | 2 |

[a]All salts are mono salts, unless specified otherwise.
NM—Not Measured

Additionally it was previously determined that pridopidine hydrochloride Form I and Form II are both deliquescent in excess of 80% RH. (WO 2013/034622).

It is generally considered undesirable to have a form with low melting point (i.e., below 100° C.), high hygroscopicity (>10% water gain at 75% RH), or multiple polymorphs. In addition, Class 1 acids are preferred over Class 2 or 3 acids. With these factors taken into account, pridopidine mono L-tartrate is ideal for development.

As discussed previously, the mono L-tartrate has high water solubility (i.e., >65 mg/mL).

Based on 4 week stress study at 40° C. and 75% RH, hydrochloride, L-malate, and L-tartrate all have acceptable chemical and physical stability. The melting point for the L-tartrate, Form A1, is higher than that of L-malate.

Example 5: Pridopidine L-tartrate, Form A1

Pridopidine L-tartrate, form A1, was analyzed by XRPD, DSC, TGA, and HPLC to monitor changes of several properties (i.e., physical form, thermal properties, and chemical purity). Pridopidine L-tartrate was compared to pridopidine hydrochloride.

As discussed in Examples 1-4 above, L-tartrate possesses overall acceptable properties (i.e. crystalline, higher melting, and less hygroscopic) for development.

Materials: A batch of pridopidine L-tartrate, a white crystalline powder, with an HPLC assay and purity of 100% for pridopidine was used. The DSC has a single thermal event with an onset at 178.2° C. and a peak max at 178.8° C. The TGA shows a weight loss of 0.03% up to 150° C. The DVS curves show surface adsorption with limited bulk absorption throughout the entire RH range. The total uptake in moisture is ~2.3%. There is no change in XRPD pattern before and after the DVS test.

Experiments and Discussion:

A nine week stability study was conducted on the L-tartrate and hydrochloride salts of pridopidine by exposing samples to 5° C., 40° C. at 75% RH, and 50° C. The samples were analyzed by XRPD, DSC/TGA, and HPLC. The results are listed in Tables 4-6.

TABLE 4

Nine Week Stability Study at 5° C.

| Storage Conditions | | 5° C.[a] | | | |
|---|---|---|---|---|---|
| | | 0 Week | 1 Week | 4 Week | 9 Week |
| Hydro-chloride, | XRPD | Form $A_1$ | Form $A_1$ | Form $A_1$ | Form $A_1$ |
| | DSC (melting point, ° C.) | 202.6 | 201.8 | 201.3 | 201.5 |
| | TGA: weight loss | 0.4 | 0.06 | 0.12 | 0.03 |
| | HPLC purity (Area %) | 99.93 | 99.92 | 99.93 | 99.91 |
| L-tartrate, | XRPD | Form $A_1$ | Form $A_1$ | Form $A_1$ | Form $A_1$ |
| | DSC (melting point, ° C.) | 178.8 | 178.9 | 178.9 | 179.2 |
| | TGA: weight loss (%) | 0.03 | 0.77 | 0.14 | 0.01 |
| | HPLC purity (Area %) | 100.00 | 100.00 | 100.00 | 100.00 |

[a]The humidity in the 5° C. chamber is monitored but not regulated. A typical value is 12% RH.

TABLE 5

Nine Week Stability Study at 40° C./75% RH

| Storage Conditions | | 40° C. and 75% RH | | | |
|---|---|---|---|---|---|
| | | 0 Week | 1 Week | 4 Week | 9 Week |
| Hydro-chloride, Batch # | XRPD | Form $A_1$ | Form $A_1$ | Form $A_1$ | Form $A_1$ |
| | DSC (melting point, ° C.) | 202.6 | 201.8 | 201.6 | 201.5 |
| | TGA: weight loss | 0.4 | 0.3 | 0.2 | 0.03 |
| | HPLC purity (Area %) | 99.93 | 99.92 | 99.93 | 99.91 |
| L-tartrate, | XRPD | Form $A_1$ | Form $A_1$ | Form $A_1$ | Form $A_1$ |
| | DSC (melting point, ° C.) | 178.8 | 179.0 | 179.7 | 179.1 |
| | TGA: weight loss | 0.03 | 0.47 | 0.01 | 0.02 |
| | HPLC purity (Area %) | 100.00 | 100.00 | 100.00 | 99.97 |

TABLE 6

Nine Week Stability Study at 50° C.

| Storage Conditions | | 50° C.[a] | | | |
|---|---|---|---|---|---|
| | | 0 Week | 1 Week | 4 Week | 9 Week |
| Hydro-chloride, | XRPD | Form $A_1$ | Form $A_1$ | Form $A_1$ | Form $A_1$ |
| | DSC (melting point, ° C.) | 202.6 | 201.3 | 201.5 | 201.5 |
| | TGA: weight loss | 0.4 | 0.27 | 0.08 | 0.10 |
| | HPLC purity (Area %) | 99.93 | 99.93 | 99.93 | 99.91 |
| L-tartrate, | XRPD | Form $A_1$ | Form $A_1$ | Form $A_1$ | Form $A_1$ |
| | DSC (melting point, ° C.) | 178.8 | 178.6 | 178.6 | 178.9 |
| | TGA: weight loss | 0.03 | 0.41 | 0.01 | 0.3 |
| | HPLC purity (Area %) | 100.00 | 100.00 | 100.00 | 100.00 |

[a]The humidity in the 50° C. chambers is monitored but not regulated. A typical value is 63% RH.

In addition, all of the stressed samples of both pridopidine salts displayed physicochemical properties comparable to the initial sample, indicating good stability. Based on the study results, L-tartrate, form A1, is as stable as the hydrochloride.

Summary, Results and Conclusion of Example 5

To evaluate physicochemical stability of pridopidine L-tartrate, Form A1, a stability study was performed. This batch the stability study was performed on was manufactured at larger scale and is representative of pridopidine L-tartrate, Form A1.

When exposed to 5° C., 40° C./75% RH, and 50° C. for 9 weeks, pridopidine Ltartrate, form A1, displayed both acceptable physical form stability (i.e. no changes in XRPD pattern, no change in thermal event in DSC, and acceptable loss on drying by TGA) and chemical stability (no detectable degradation by HPLC). Its stability was comparable to pridopidine hydrochloride, form A1. Pridopidine L-tartrate, Form A1, is confirmed to be acceptable in terms of physicochemical stability and is comparable to pridopidine hydrochloride, Form A1.

Example 6: Pridopidine L-tartrate Structure

The calculated X-ray pattern after Rietveld refinement compares well to the measured pattern (FIG. 1 and Table 8). The crystal structures of pridopidine L-tartrate has been determined by single crystal x-ray diffraction methods. The packing in the L-tartrate salt is comprised of layers of pridopidine anions and columns of tartrate cations.

The single crystal structure of pridopidine L-tartrate is shown in FIG. 8. The packing of pridopidine L-tartrate is shown in FIG. 9. The chirality of the L-tartrate anion is confirmed by the single crystal x-ray structure.

TABLE 8

X-ray Diffraction Peak Information for pridopidine tartrate

| Pos. [°2 Th.] | Position calc. | h | k | l | Height [cts] | Rel. Int. [%] | d-space value |
|---|---|---|---|---|---|---|---|
| 10.39 | 10.36 | 0 | 0 | 1 | 4335 | 53.1 | 8.5067 |
| 10.78 | 10.75 | 1 | 0 | 0 | 562 | 6.9 | 8.2032 |
| 12.28 | 12.25 | 1 | 1 | 0 | 721 | 8.8 | 7.2023 |
| 14.38 | 14.35 | 1 | 0 | −1 | 1845 | 22.6 | 6.1530 |
| 15.55 | 15.52 | 1 | 0 | 1 | 8101 | 99.3 | 5.6937 |

TABLE 8-continued

X-ray Diffraction Peak Information for pridopidine tartrate

| Pos. [°2 Th.] | Position calc. | h | k | l | Height [cts] | Rel. Int. [%] | d-space value |
|---|---|---|---|---|---|---|---|
| 15.71 | 15.68 | 0 | 2 | −1 | 864 | 10.6 | 5.6359 |
| 16.63 | 16.60 | 1 | 1 | 1 | 502 | 6.2 | 5.3254 |
| 18.61 | 18.58 | 1 | 2 | −1 | 2863 | 35.1 | 4.7636 |
| 19.53 | 19.50 | 1 | 2 | 1 | 1166 | 14.3 | 4.5408 |
| 20.74 | 20.71 | 1 | 3 | 0 | 2087 | 25.6 | 4.2801 |
| 20.84 | 20.81 | 0 | 0 | 2 | 8162 | 100.0 | 4.2597 |
| 21.62 | 21.59 | 2 | 0 | 0 | 427 | 5.2 | 4.1076 |
| 21.66 | 21.63 | 0 | 1 | 2 | 1123 | 13.8 | 4.0988 |
| 22.74 | 22.70 | 1 | 0 | −2 | 1395 | 17.1 | 3.9080 |
| 22.85 | 22.82 | 1 | 3 | −1 | 1271 | 15.6 | 3.8887 |
| 23.28 | 23.25 | 2 | 0 | −1 | 1153 | 14.1 | 3.8182 |
| 23.50 | 23.47 | 1 | 1 | −2 | 360 | 4.4 | 3.7827 |
| 23.98 | 23.95 | 0 | 2 | −2 | 543 | 6.7 | 3.7073 |
| 24.03 | 23.99 | 2 | 1 | −1 | 2289 | 28.0 | 3.7010 |
| 24.76 | 24.73 | 2 | 0 | 1 | 224 | 2.8 | 3.5932 |
| 24.97 | 24.94 | 1 | 1 | 2 | 359 | 4.4 | 3.5636 |
| 25.46 | 25.43 | 2 | 1 | 1 | 386 | 4.7 | 3.4950 |
| 25.66 | 25.63 | 1 | 2 | −2 | 287 | 3.5 | 3.4685 |
| 26.03 | 26.00 | 1 | 4 | 0 | 509 | 6.2 | 3.4206 |
| 27.02 | 26.99 | 1 | 2 | 2 | 204 | 2.5 | 3.2973 |
| 27.44 | 27.41 | 0 | 3 | −2 | 424 | 5.2 | 3.2477 |
| 27.48 | 27.45 | 2 | 2 | 1 | 240 | 2.9 | 3.2428 |
| 28.05 | 28.02 | 2 | 3 | 0 | 1034 | 12.7 | 3.1787 |
| 28.93 | 28.90 | 1 | 3 | −2 | 251 | 3.1 | 3.0835 |
| 29.37 | 29.34 | 2 | 3 | −1 | 409 | 5.0 | 3.0388 |
| 30.57 | 30.54 | 2 | 3 | 1 | 194 | 2.4 | 2.9217 |
| 31.46 | 31.43 | 0 | 0 | 3 | 391 | 4.8 | 2.8413 |
| 33.09 | 33.06 | 1 | 5 | −1 | 259 | 3.2 | 2.7048 |
| 33.60 | 33.57 | 2 | 2 | 2 | 177 | 2.2 | 2.6652 |
| 34.68 | 34.65 | 1 | 1 | 3 | 246 | 3.0 | 2.5845 |
| 35.66 | 35.63 | 3 | 1 | 1 | 233 | 2.9 | 2.5156 |

Discussion:

One of the many steps in the drug development process is identifying a solid form of the drug which can serve as an effective drug product. The formulation must be effective at delivering the active molecule to the targeted bio system (Newman 2002). Reaction of bioactive organic molecules with acids or bases produce salts, which have different physical properties than the base compound (Newman 2002). One important property of a drug substance is its hygroscopicity (Newman 2002).

The physical properties of a salt, including an L-tartrate salt, of a compound, such as hygroscopicity, cannot be predicted. For example, the literature has examples of an L-tartrate salt sometimes being hygroscopic and sometimes being non-hygroscopic. For instance, an L-tartrate salt described in Anton, 2003 and U.S. Pat. No. 6,271,258 is non-hygroscopic. In comparison, the L-tartrate salts described in US Patent Publication No. 2012/0035212 and Zolpidemi Tartras, European Pharmacopoeia, 2014 are hygroscopic.

Properties of different forms of pridopidine hydrochloride were published. (Zimmermann 2012) Forms of pridopidine are also discussed in International Publication No. WO 2013/034622.

The hydrochloride salt of pridopidine disclosed in WO 01/46145 is non-hygroscopic at relative humidities below 86%, but deliquescent in excess of 86% relative humidity. This means that the salt is able to take up so much moisture from the surroundings that the salt is dissolved. The claimed invention retains the same therapeutic properties as the hydrochloride salt previously disclosed, yet is substantially non-hygroscopic up to at least 90% relative humidity. This is unexpected and could not have been predicted from earlier published studies.

The L-tartrate salt of pridopidine has been found to possess ideal properties. The L-tartrate salt of pridopidine has ideal hydroscopicity at all humidity levels, in particular at 90% relative humidity, especially when compared to all other pridopidine salts as a whole. The L-tartrate salt of pridopidine only forms one polymorph and is a class 1 acid, which is preferred over class 2 or class 3 acids. The L-tartrate of pridopidine also has an ideal melting point and an acceptable solubility in water. The broad range of properties of the different pridopidine salts shows that the specific properties of the L-tartrate salt are ideal and could not have been predicted.

REFERENCES CITED

R. Anton, S. Barlow, D. Boskou, L. Castle, R. Crebelli, W. Dekant, K.-H Engel, S. Forsythe, W. Grunow, J.-C. Larsen, C. Leclercq, W. Mennes, M.-R. Milana, I. Rietjens, K. Svensson, P. Tobback, F. Toldrá. Opinion of the Scientific Panel on Food Additives, Flavourings, Processing Aids and Materials in Contact with Food (AFC) on a request from the Commission related to L-Carnitine-L-tartrate for use in foods for particular nutritional uses. The EFSA. Journal (2003)19, 1-13.

Mahant N, McCusker E A, Byth K, Graham S; Huntington Study Group. Huntington's disease: clinical correlates of disability and progression. Neurology. 2003 Oct. 28; 61(8):1085-92.

Nieoullon A, Coquerel A. Dopamine: a key regulator to adapt action, emotion, motivation and cognition, Curr Opin Neurol. 2003 Dec. 16 Suppl 2:S3-9.

Zhan L, Kerr J R, Lafuente M J, Maclean A, Chibalina M V, Liu B, Burke B, Bevan S, Nasir J. Altered expression and coregulation of dopamine signalling genes in schizophrenia and bipolar disorder. Neuropathol Appl Neurobiol. 2011 February; 37(2):206-19.

Dunlop B W, Nemeroff C B. The role of dopamine in the pathophysiology of depression. Arch Gen Psychiatry. 2007 March; 64(3):327-37.

Kung V W, Hassam R, Morton A J, Jones S. Dopamine-dependent long term potentiation in the dorsal striatum is reduced in the R6/2 mouse model of Huntington's disease. Neuroscience. 2007 Jun. 3; 146(4):1571-30.

Huot P, Lévesque M, Parent A. The fate of striatal dopaminergic neurons in Parkinson's disease and Huntington's chorea. Brain. 2007 January; 130(Pt 1):222-32.

Mestre T, Ferreira J, Coelho M M, Rosa M, Sampaio C. Therapeutic interventions for disease progression in Huntington's disease. Cochrane Database Syst Rev. 2009 Jul. 8; (3):CD006455.

Mestre T, Ferreira J, Coelho M M, Rosa M, Sampaio C. Therapeutic interventions for symptomatic treatment in Huntington's disease. Cochrane Database Syst Rev. 2009 Jul. 8; (3):CD006456.

Newman and Stably, "Form Selection of Pharmaceutical Compounds," in Handbook of Pharmaceutical Analysis, Marcel Dekker, Inc, (2002).

Ponten H, Kullingsjö J, Lagerkvist S, Martin P, Pettersson F, Sonesson C, Waters S, Waters N. In vivo pharmacology of the dopaminergic stabilizer pridopidine. Eur J Pharmacol. 2010 Oct. 10; 644(1-3):33-95.

Zimmermann, A; Frostrup, B; Bond, A D. Polymorphs of Priopidine Hydrochloride. Cryst. Growth Des, 2012, 12, 2961-2968

Zolpidemi tartras, EUROPEAN PHARMACOPOEIA 5.0, Monographs T-Z, 2734, 01/2005:1280, date of access: Dec. 8, 2014

The invention claimed is:

1. Pridopidine L-tartrate, characterized by a XRPD pattern with reflections corresponding to the d-spacing values 8.5±0.1, 4.8±0.1, 4.3±0.1, and 3.7±0.1, wherein the pridopidine L-tartrate is in crystalline form A1.

2. The pridopidine L-tartrate of claim 1, which is pridopidine mono L-tartrate.

3. The pridopidine L-tartrate of claim 1 characterized by a XRPD pattern with reflections corresponding to the d-spacing values 8.5±0.1, 6.2±0.1, 5.7±0.1, 4.8±0.1, 4.5±0.1, 4.3±0.1, 4.1±0.1, 3.9±0.1, 3.8±0.1, 3.7±0.1, and 3.2±0.1, wherein the pridopidine L-tartrate is in crystalline form A1.

4. The pridopidine L-tartrate of claim 1 which is isolated.

5. A composition comprising the pridopidine L-tartrate of claim 1, and a carrier.

6. A composition comprising the pridopidine L-tartrate of claim 1, wherein the composition is free of L-tartaric acid.

7. A composition comprising the pridopidine L-tartrate of claim 1, wherein the composition has less than 5% L-tartaric acid by weight.

8. The composition of claim 5, further comprising pridopidine base.

9. The composition of claim 8, wherein the pridopidine base is present in an amount of less than 5% based on total pridopidine content of the composition.

10. The composition of claim 5, which is free of pridopidine base.

11. The composition of claim 5, wherein the composition has less than 5% pridopidine base by weight.

12. The composition of claim 5, wherein the composition is a pharmaceutical composition and the carrier is a pharmaceutically acceptable carrier.

13. The pharmaceutical composition of claim 12, which is in tablet form.

14. The pharmaceutical composition of claim 13, wherein the tablet unit form comprises between 22.5-315 mg pridopidine or between 90-315 mg pridopidine.

15. The pharmaceutical composition of claim 13, wherein the tablet unit form comprises about 22.5 mg, about 45 mg, about 67.5 mg, about 90 mg, about 100 mg, about 112.5 mg, about 125 mg, about 135 mg, about 150 mg, about 180 mg, about 200 mg, about 250 mg, or about 315 mg pridopidine.

16. The pharmaceutical composition of claim 13, wherein the tablet unit form is prepared for once daily administration.

17. The pharmaceutical composition of claim 13, wherein the tablet unit form is prepared for more than once daily administration.

18. A process for manufacture of the pridopidine L-tartrate of claim 1 comprising:
   a) combining L-tartaric acid with pridopidine free base to form a mixture
   b) obtaining pridopidine L-tartrate from the mixture.

19. A method of treating a human subject afflicted with Huntington's disease comprising administering to the human subject an amount of the pridopidine L-tartrate of claim 1 effective to treat the human subject.

* * * * *